United States Patent
Boutet

(10) Patent No.: US 11,926,863 B1
(45) Date of Patent: Mar. 12, 2024

(54) SOLID STATE SINGLE CELL METHOD FOR ANALYZING FIXED BIOLOGICAL CELLS

(71) Applicant: 10X Genomics, Inc., Pleasanton, CA (US)

(72) Inventor: Stephane Claude Boutet, Burlingame, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 457 days.

(21) Appl. No.: 17/187,227

(22) Filed: Feb. 26, 2021

Related U.S. Application Data

(60) Provisional application No. 62/982,495, filed on Feb. 27, 2020.

(51) Int. Cl.
*C12Q 1/68* (2018.01)
*C12Q 1/6804* (2018.01)
*C12Q 1/6806* (2018.01)

(52) U.S. Cl.
CPC ......... *C12Q 1/6806* (2013.01); *C12Q 1/6804* (2013.01); *C12Q 2565/514* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |

(Continued)

FOREIGN PATENT DOCUMENTS

| | | |
|---|---|---|
| CN | 1680604 | 10/2005 |
| EP | 1923471 | 5/2008 |

(Continued)

OTHER PUBLICATIONS

Adam et al., "Psychrophilic proteases dramatically reduce single-cell RNA-seq artifacts: a molecular atlas of kidney development," Development, Oct. 1, 2017, 144(19):3625-3632.

(Continued)

*Primary Examiner* — Aaron A Priest
(74) *Attorney, Agent, or Firm* — Fish & Richardson P.C.

(57) ABSTRACT

A method of analyzing single biological particles, such as cells or nuclei, that maintains the single biological particles in a state of relative isolation during decrosslinking and subsequent processing is provided. In the case of cells, the method prevents cellular analytes from each individual cell from leaving the cell site and diffusing toward adjacent cells, while permitting transmission of a decrosslinking agent, followed by processing of the cellular analytes from the individual cells by barcoding and/or imaging of the cellular analytes.

19 Claims, 5 Drawing Sheets

(56) References Cited

U.S. PATENT DOCUMENTS

| | | |
|---|---|---|
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,258,568 B1 | 7/2001 | Nyren |
| 6,266,459 B1 | 7/2001 | Walt |
| 6,274,320 B1 | 8/2001 | Rothberg |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,897,023 B2 | 5/2005 | Fu |
| 6,942,968 B1 | 9/2005 | Dickinson et al. |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,211,414 B2 | 5/2007 | Hardin |
| 7,255,994 B2 | 8/2007 | Lao |
| 7,258,976 B2 | 8/2007 | Mitsuhashi |
| 7,297,518 B2 | 11/2007 | Quake |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,582,420 B2 | 9/2009 | Oliphant et al. |
| 7,601,498 B2 | 10/2009 | Mao |
| 7,635,566 B2 | 12/2009 | Brenner |
| 7,674,752 B2 | 3/2010 | He |
| 7,776,547 B2 | 8/2010 | Roth |
| 7,776,567 B2 | 8/2010 | Mao |
| 7,803,943 B2 | 9/2010 | Mao |
| 7,910,304 B2 | 3/2011 | Drmanac |
| 7,955,794 B2 | 6/2011 | Shen et al. |
| 7,960,119 B2 | 6/2011 | Chee |
| 8,003,354 B2 | 8/2011 | Shen et al. |
| 8,148,068 B2 | 4/2012 | Brenner |
| 8,206,917 B2 | 6/2012 | Chee |
| 8,288,103 B2 | 10/2012 | Oliphant |
| 8,288,122 B2 | 10/2012 | O'Leary et al. |
| 8,343,500 B2 | 1/2013 | Wraith |
| 8,460,865 B2 | 6/2013 | Chee |
| 8,481,257 B2 | 7/2013 | Van Eijk |
| 8,603,743 B2 | 12/2013 | Liu et al. |
| 8,815,512 B2 | 8/2014 | Van Eijk |
| 8,835,358 B2 | 9/2014 | Fodor |
| 8,911,945 B2 | 12/2014 | Van Eijk |
| 9,062,348 B1 | 6/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,404,156 B2 | 8/2016 | Hicks |
| 9,506,061 B2 | 11/2016 | Brown et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,727,810 B2 | 8/2017 | Fodor et al. |
| 9,777,324 B2 | 10/2017 | Van Eijk |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 9,902,950 B2 | 2/2018 | Church et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,208,982 B2 | 2/2019 | Bannish et al. |
| 10,266,876 B2 | 4/2019 | Cai et al. |
| 10,267,808 B2 | 4/2019 | Cai |
| 10,273,541 B2 | 4/2019 | Hindson et al. |
| 10,357,771 B2 | 7/2019 | Bharadwaj |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,590,244 B2 | 3/2020 | Delaney et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |

(56) References Cited

U.S. PATENT DOCUMENTS

| | | |
|---|---|---|
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 2002/0040275 A1 | 4/2002 | Cravatt |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0087232 A1 | 5/2003 | Christians |
| 2003/0148335 A1 | 8/2003 | Shen et al. |
| 2003/0162216 A1 | 8/2003 | Gold |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0096853 A1 | 5/2004 | Mayer |
| 2004/0106110 A1 | 6/2004 | Balasubramanian |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2006/0046313 A1 | 3/2006 | Roth |
| 2006/0211001 A1 | 9/2006 | Yu et al. |
| 2006/0216775 A1 | 9/2006 | Burkart et al. |
| 2006/0263789 A1 | 11/2006 | Kincaid |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0009420 A1 | 1/2008 | Schroth et al. |
| 2008/0108804 A1 | 5/2008 | Hayashizaki et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0289184 A1 | 11/2009 | Deininger |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0120097 A1 | 5/2010 | Matz et al. |
| 2010/0120098 A1 | 5/2010 | Grunenwald et al. |
| 2010/0145037 A1 | 6/2010 | Brive et al. |
| 2011/0028685 A1 | 2/2011 | Purkayastha et al. |
| 2011/0059436 A1 | 3/2011 | Hardin et al. |
| 2011/0223613 A1 | 9/2011 | Gut |
| 2011/0245111 A1 | 10/2011 | Chee |
| 2012/0010091 A1 | 1/2012 | Linnarson |
| 2012/0135871 A1 | 5/2012 | van Eijk et al. |
| 2012/0202698 A1 | 8/2012 | van Eijk et al. |
| 2014/0065609 A1 | 3/2014 | Hicks et al. |
| 2014/0066318 A1 | 3/2014 | Frisen et al. |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0378350 A1 | 12/2014 | Hindson et al. |
| 2015/0292988 A1 | 10/2015 | Bharadwaj et al. |
| 2015/0344942 A1 | 12/2015 | Frisen et al. |
| 2016/0032282 A1 | 2/2016 | Vigneault et al. |
| 2016/0138091 A1 | 5/2016 | Chee et al. |
| 2016/0145677 A1 | 5/2016 | Chee et al. |
| 2016/0201125 A1 | 7/2016 | Samuels et al. |
| 2016/0253584 A1* | 9/2016 | Fodor .................. C12Q 1/6813 235/494 |
| 2016/0289669 A1 | 10/2016 | Fan et al. |
| 2016/0289740 A1* | 10/2016 | Fu ........................ C12Q 1/6806 |
| 2016/0298180 A1 | 10/2016 | Chee |
| 2017/0283860 A1 | 4/2017 | Kool et al. |
| 2017/0159109 A1* | 6/2017 | Zheng .................. C12Q 1/6809 |
| 2017/0220733 A1 | 8/2017 | Zhuang et al. |
| 2017/0242020 A1 | 8/2017 | Yamauchi et al. |

(56) References Cited

U.S. PATENT DOCUMENTS

| | | |
|---|---|---|
| 2017/0342405 A1 | 11/2017 | Fu et al. |
| 2017/0343545 A1 | 11/2017 | Hadrup et al. |
| 2018/0057873 A1 | 3/2018 | Zhou et al. |
| 2018/0080019 A1 | 3/2018 | Blainey et al. |
| 2018/0105808 A1 | 4/2018 | Mikkelsen et al. |
| 2018/0112261 A1 | 4/2018 | Van Driel et al. |
| 2018/0114316 A1 | 4/2018 | Lele et al. |
| 2018/0201980 A1 | 7/2018 | Chee et al. |
| 2018/0216162 A1 | 8/2018 | Belhocine et al. |
| 2018/0245142 A1* | 8/2018 | So ................. C12Q 1/6837 |
| 2018/0251825 A1 | 9/2018 | Stoeckius et al. |
| 2018/0282803 A1 | 10/2018 | Belgrader et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0346970 A1 | 12/2018 | Chang |
| 2019/0064173 A1 | 2/2019 | Bharadwaj et al. |
| 2019/0085324 A1 | 3/2019 | Regev et al. |
| 2019/0135774 A1 | 5/2019 | Orbai |
| 2019/0144936 A1* | 5/2019 | Gierahn ............. B01J 19/0046 506/4 |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0203275 A1 | 7/2019 | Frisen et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0352708 A1 | 11/2019 | Gaige et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0002764 A1 | 1/2020 | Belgrader et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0109443 A1 | 4/2020 | Chee |
| 2020/0173985 A1 | 6/2020 | Dong et al. |
| 2020/0256867 A1 | 8/2020 | Hennek et al. |
| 2020/0277663 A1 | 9/2020 | Iyer |
| 2020/0277664 A1* | 9/2020 | Frenz ................. C12Q 1/6874 |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1* | 6/2021 | Tentori ................. C12Q 1/6841 |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0315984 A1 | 10/2022 | Edelman et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |

(56) References Cited

U.S. PATENT DOCUMENTS

| | | |
|---|---|---|
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403374 A1 | 12/2022 | Soumillon |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |

FOREIGN PATENT DOCUMENTS

| | | |
|---|---|---|
| EP | 2002017 | 12/2008 |
| EP | 2881465 | 6/2015 |
| EP | 3013984 | 5/2016 |
| EP | 3511423 | 7/2019 |
| EP | 3541956 | 9/2019 |
| RU | 2270254 | 2/2006 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2000/017390 | 3/2000 |
| WO | WO 2000/024940 | 5/2000 |
| WO | WO 2000/063437 | 10/2000 |
| WO | WO 2002/024952 | 3/2002 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2005/007814 | 1/2005 |
| WO | WO 2006/117541 | 11/2006 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2009/152928 | 12/2009 |
| WO | WO 2010/126614 | 11/2010 |
| WO | WO 2011/008502 | 1/2011 |
| WO | WO 2011/068088 | 6/2011 |
| WO | WO 2011/094669 | 8/2011 |
| WO | WO 2012/048341 | 4/2012 |
| WO | WO 2012/083225 | 6/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/210223 | 12/2014 |
| WO | WO 2015/031691 | 3/2015 |
| WO | WO 2015/188839 | 12/2015 |
| WO | WO 2016/040476 | 3/2016 |
| WO | WO 2016/057552 | 4/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/013170 | 1/2017 |
| WO | WO 2017/019456 | 2/2017 |
| WO | WO 2017/075265 | 5/2017 |
| WO | WO 2017/075293 | 5/2017 |
| WO | WO 2017/096158 | 7/2017 |
| WO | WO 2017/147483 | 8/2017 |
| WO | WO 2018/064640 | 4/2018 |
| WO | WO 2018/075693 | 4/2018 |
| WO | WO 2018/091676 | 5/2018 |
| WO | WO 2018/175779 | 9/2018 |
| WO | WO 2019/104337 | 5/2019 |
| WO | WO 2019/113457 | 6/2019 |
| WO | WO 2019/113533 | 6/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047010 | 3/2020 |
| WO | WO 2020/076979 | 4/2020 |
| WO | WO 2020/077236 | 4/2020 |
| WO | WO 2020/099640 | 5/2020 |
| WO | WO 2020/123301 | 6/2020 |
| WO | WO 2020/123305 | 6/2020 |
| WO | WO 2020/123311 | 6/2020 |

(56) References Cited

FOREIGN PATENT DOCUMENTS

| | | |
|---|---|---|
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/227309 | 11/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |

OTHER PUBLICATIONS

Eastburn et al., "Identification of Genetic Analysis of Cancer Cells with PCT-activated Cell Sorting," Nucleic Acids Research, Jul. 16, 2014, 42(16):e128, 10 pages.

Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.

Edsgard et al., "Identification of spatial expression trends in single-cell gene expression data," Nature Methods, Mar. 19, 2018, 15: 339-342, 16 pages.

Ha et al., "Self-assembly hollow nanosphere for enzyme encapsulation," Soft Matter, Feb. 11, 2010, 6, 1405-1408, 10 pages.

Hu et al., "A thermo-degradable hydrogel with light-tunable degradation and drug release," Biomaterials, Jan. 2017, 112:133-140.

Ju et al, "Supramolecular dendrimer capsules by cooperative binding," Chem. Commun., Jan. 7, 2011, 47(1):268-270, 8 pages.

Kuiper et al, "Enzymes containing porous polymersomes as nano reaction vessels for cascade reactions," Org. Biomol, Chem, Oct. 15, 2008, 6(23):4315-4318.

Liu et al., "Preparation and Characterization of Temperature-Sensitive Poly(N-isopropylacrylamide)-b-poly(d,1-lactide) Microspheres for Protein Delivery," Biomacromolecules, 2003, 4(6):1784-1793.

Luo et al., "Probing infectious disease by single-cell RNA sequencing: Progresses and perspectives," Computational and Structural Biotechnology Journal, Oct. 21, 2020, 18:2962-2971.

Lyu et al., "One-Pot Synthesis of Protein-Embedded Metal-Organic Frameworks with Enhanced Biological Activities," Nano Lett., Sep. 11, 2014, 14:5761-5765.

Massoni-Badosa et al, "Sampling artifacts in single-cell genomics cohort studies," bioRxiv, Jan. 15, 2020, 32 pages.

Miller et al., "Rapid and Efficient Enzyme Encapsulation in a Dendrimer Silica Nanocomposite," Macromolecular Bioscience, Oct. 25, 2006, 6(10):839-845.

O'Flanagan et al., "Dissociation of solid tumor tissues with cold active protease for single-cell RNA-seq minimizes conserved collagenase-associated stress responses," Genome Biology, Oct. 17, 2019, 20:210, 13 pages.

Pellegrino et al, "High-throughput Single-cell DNA Sequencing of Acut Myeloid Leukemia Tumors with Droplet Microfluidics, " Genome Research, Aug. 7, 2018, 28(9):1345-1352.

Rahimi et al, "Synthesis and Characterization of Thermo-Sensitive Nanoparticles for Drug Delivery Applications," J. Biomed. Nanotechnol. Dec. 2008, 4(4):482-490, 19 pages.

Shieh, et al., "Imparting Functionality to Biocatalysts via Embedding Enzymes into Nanoporous Materials by a de Novo Approach: Size-Selective Sheltering of Catalase in Metal-Organic Framework Microcrystals," J Am Chem Soc., Apr. 8, 2015, 137(13):4276-4279, 4 pages.

Soderberg, "Droplet Microfluidics Reverse Transcription and PCR Towards Single Cell and Exosome Analysis," Doctoral Thesis, KTH School of Biotechnology Science for Life Laboratory, 2017, 69 pages.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

Pittcon, "Single Molecule Detection of Proteins in Single Cells," News-Medical, Feb. 3, 2017, retreived on Nov. 1, 2023, retrieved from URL <https://www.news-medical.net/news/20170203/Single-molecule-detection-of-proteins-in-single-cells.aspx>, 13 pages.

Redmond et al., "Single-cell TCRseq: paired recovery of entire T-cell alpha and beta chain transcripts in T-cell receptors from single-cell RNAseq," Genome Med, 2016, 8:80, 12 pages.

Tang et al., "mRNA-Seq whole-transcriptome analysis of a single cell," Nat Methods, 2009, 6:377-382.

O'Huallachain et al., "Ultra-high throughput single-cell analysis of proteins and RNAs by split-pool synthesis," Communications Biology, 2020, 3:213, 19 pages.

Satija et al., "Spatial reconstruction of single-cell gene expression data," Nature, Apr. 13, 2015, 33(5):495-402, 14 pages.

Stoeckius et al., "Simultaneous epitope and transcriptome measurement in single cells," Nature Methods, Jul. 31, 2017, 14(9):865-868.

(56) References Cited

OTHER PUBLICATIONS

U.S. Appl. No. 16/353,937, filed Mar. 14, 2019, Frisen et al.
U.S. Appl. No. 17/707,189, filed Mar. 29, 2022, Chell et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms, " Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Armani et al, "2D-PCR: a method of mapping DNA in tissue sections," Lab Chip, 2009, 9(24):3526-34.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bergenstråhle et al., "Seamless integration of image and molecular analysis for spatial transcriptomics workflows," BMC Genomics, Jul. 2020, 21(1):482, 7 pages.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.

(56) References Cited

OTHER PUBLICATIONS

Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "ATAC-see reveals the accessible genome by transposase-mediated imaging and sequencing," Nature Methods, Dec. 2016, 13(12):1013-1020.
Chen et al., "Geometric control of cell life and death," Science, May 1997, 276(5317):1425-1428.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Cho et al., "Seq-Scope: Submicrometer-resolution spatial transcriptomics for single cell and subcellular studies," bioRxiv, Jan. 27, 2021, retrieved from URL<https://www.biorxiv.org/node/1754517.abstract>, 50 pages.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Codeluppi et al., "Spatial organization of the somatosensory cortex revealed by osmFISH," Nature Methods, Nov. 2018, 15:932-935.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring," Life Science News, Amersham Life Science, 1998, pp. 11-14.
Corces et al., "Lineage-specific and single-cell chromatin accessibility charts human hematopoiesis and leukemia evolution," Nature Genetics, Oct. 2016, 48(10):1193-1203.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60- 6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Datlinger et al., "Pooled CRISPR screening with single-cell transcriptome readout," Nat Methods, Mar. 2017, 14(3):297-301.

Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
DePasquale et al., "DoubletDecon: Deconvoluting Doublets from Single-Cell RNA-Sequencing Data," Cell Rep., Nov. 5, 2019, 29(6):1718-1727.e8, 19 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Duncan et al., "Affinity chromatography of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Falconnet et al., "Surface engineering approaches to micropattern surfaces for cell-based assays," Biomaterials, Jun. 2006, 27(16):3044-3063.
Fire et al., "Rolling replication of short DNA circles," Proc. Natl. Acad. Sci., 1995, 92(10):4641-4645.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.

(56) References Cited

OTHER PUBLICATIONS

Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gross et al., "Technologies for Single-Cell Isolation," Int. J Mol. Sci., Jul. 2015, 16(8):16897-16919.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS One, 2012, 7(7):e40405, 9 pages.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing," PLoS One, 5(7): e11345, 2010.
Hejatko et al., "In situ hybridization technique for mRNA detection in whole mount *Arabidopsis* samples, " Nature Protocols, 2006, 1(4):1939-1946.
Hiatt et al., "Parallel, tag-directed assembly of locally derived short sequence reads," Nature Methods, 2010, 7(2):119-25.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hughes et al., "Highly Efficient, Massively-Parallel Single-Cell RNA-Seq Reveals Cellular States and Molecular Features of Human Skin Pathology," bioRxiv, Jul. 2019, 51 pages.
Jabara et al., Accurate sampling and deep sequencing of the HIV-1 protease gene using a Primer ID. PNAS 108(50); 20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jones et al., "Comparative lesion sequencing provides insights into tumor evolution," Proc. Natl. Acad. Sci. USA, 105(11): 4283-4288, 2008.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.
Kozlov et al., "A highly scalable peptide-based assay system for proteomics," PLoS One, 2012, 7(6):e37441, 10 pages.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Laurell et al., "Chip integrated strategies for acoustic separation and manipulation of cells and particles," Chem. Soc. Rev., Mar. 2007, 36(3):492-506.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Liberali et al., "Single-cell and multivariate approaches in genetic perturbation screens," Nat Rev Genet., Jan. 2015, 16(1):18-32.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lundberg et al., "Multiplexed homogeneous proximity ligation assays for high-throughput protein biomarker research in serological material," Mol Cell Proteomics, 2011, 10(4):M110.004978, 11 pages.

(56) References Cited

OTHER PUBLICATIONS

MacBeath et al., "Printing proteins as microarrays for high-throughput function determination," Science, Sep. 2000, 289(5485):1760-1763.

Macosko et al., "Highly Parallel Genome-wide Expression Profiling of Individual Cells Using Nanoliter Droplets," Cell, 2015, 161:1202-1214.

Madissoon et al., "scRNA-seq assessment of the human lung, spleen, and esophagus tissue stability after cold preservation," Genome Biol., Dec. 2019, 21(1):1, 16 pages.

McGinnis et al., "MULTI-seq: sample multiplexing for single-cell RNA sequencing using lipid-tagged indices," Nat Methods, Jul. 2019, 16(7): 619-626, 14 pages.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miller et al., "Basic concepts of microarrays and potential applications in clinical microbiology," Clinical Microbiology Reviews, 2009, 22(4):611-633.

Miller et al., "Chapter 11—Solid and Suspension Microarrays for Microbial Diagnostics," Methods in Microbiology, 2015, 42:395-431.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mizusawa et al., "A bacteriophage lambda vector for cloning with BamHI and Sau3A," Gene, 1982, 20(3):317-322.

Mortazavi et al., "Mapping and quantifying mammalian transcriptomes by RNA-Seq," Nature Methods, 5(7): 621-8, 2008.

Nakamura et al., "Biocompatible inkjet printing technique for designed seeding of individual living cells," Tissue Eng, Nov. 2005, 11(11-12):1658-1666.

Nam et al., "Somatic mutations and cell identity linked by Genotyping of Transcriptomes," Nature, Jul. 2019, 571(7765):355-360.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Nikiforov et al., "The use of 96-well polystyrene plates for DNA hybridization-based assays: an evaluation of different approaches to oligonucleotide immobilization," Anal Biochem, May 1995, 227(1):201-9.

Nowak et al., "Entering the Postgenome Era," Science, 1995, 270(5235):368-71.

Ostuni et al., "Patterning Mammalian Cells Using Elastomeric Membranes," Langmuir, Aug. 2000, 16(20):7811-7819.

PCT International Preliminary Report on Patentability in International Appln. No. PCT/EP2016/057355, dated Oct. 10, 2017, 7 pages.

PCT International Preliminary Report on Patentability in International Appln. No. PCT/US2021/018795, dated Sep. 1, 2022, 10 pages.

PCT International Preliminary Report on Patentability in International Appln. No. PCT/US2021/018816, dated Sep. 1, 2022, 9 pages.

PCT International Search Report and Written Opinion in International Appln. No. PCT/US2022/028071, dated Aug. 25, 2022, 13 pages.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Picelli et al., "Full-length RNA-seq from single cells using Smart-seq2," Nat Protoc., Jan. 2014, 9(1):171-81.

Polsky-Cynkin et al., "Use of DNA immobilized on plastic and agarose supports to detect DNA by sandwich hybridization," Clin. Chem., 1985, 31(9):1438-1443.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Rettig et al., "Large-scale single-cell trapping and imaging using microwell arrays," Anal Chem, Sep. 2005, 77(17):5628-5634.

Rodriques et al., "Slide-seq: A scalable technology for measuring genome-wide expression at high spatial resolution," Science, 2019, 363(6434):1463-1467.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Rosenthal et al., "Cell patterning chip for controlling the stem cell microenvironment," Biomaterials, Jul. 2007, 28(21):3208-3216.

Salmén et al., "Barcoded solid-phase RNA capture for Spatial Transcriptomics profiling in mammalian tissue sections," Nature Protocols, Oct. 2018, 13(11):2501-2534.

Satpathy et al., "Massively parallel single-cell chromatin landscapes of human immune cell development and intratumoral T cell exhaustion," Nat Biotechnol., Aug. 2019, 37(8):925-936.

Saxonov et al., "10x Genomics, Mastering Biology to Advance Human Health," PowerPoint, 10x, 2020, 41 pages.

Schena et al., "Quantitative monitoring of gene expression patterns with a complementary DNA microarray," Science, Oct. 1995, 270(5235):467-470.

Setliff et al., High-Throughput Mapping of B Cell Receptor Sequences to Antigen Specificity, Cell, 2019, 179:1636-1646.

Shalon et al., "A DNA microarray system for analyzing complex DNA samples using two-color fluorescent probe hybridization," Genome Res., Jul. 1996, 6(7):639-45.

Shirai et al., "Novel Tools for Analyzing Gene Expressions in Single Cells," The 5th International Workshop on Approaches to Single-Cell Analysis, The University of Tokyo, Mar. 3-4, 2011, 1 page.

Singh et al., "High-throughput targeted long-read single cell sequencing reveals the clonal and transcriptional landscape of lymphocytes," Nat Commun., Jul. 2019, 10(1):3120, 13 pages.

Skene et al., "An efficient targeted nuclease strategy for high-resolution mapping of DNA binding sites," Elife, Jan. 2017, 6:e21856, 35 pages.

Sountoulidis et al., "SCRINSHOT, a spatial method for single-cell resolution mapping of cell states in tissue sections," PLoS Biol., Nov. 2020, 18(11):e3000675, 32 pages.

Stahl et al., "Visualization and analysis of gene expression in tissue sections by spatial transcriptomics," Science, Jul. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Stoeckius et al., "Cell Hashing with barcoded antibodies enables multiplexing and doublet detection for single cell genomics," Genome Biology, Dec. 19, 2018, 19: 224, 12 pages.

Strell et al., "Placing RNA in context and space—methods for spatially resolved transcriptomics," The FEBS Journal, 2019, 286(8):1468-1481.

Stuart et al., "Comprehensive Integration of Single-Cell Data," Cell, Jun. 2019, 177(7):1888-1902.

(56) References Cited

OTHER PUBLICATIONS

Suh et al., "A simple soft lithographic route to fabrication of poly(ethylene glycol) microstructures for protein and cell patterning," Biomaterials, Feb. 2004, 25(3):557-563.
Takei et al., "Integrated Spatial Genomics Reveals Global Architecture Of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Tentori et al., "Detection of Isoforms Differing by a Single Charge Unit in Individual Cells," Chem. Int. Ed., 2016, 55(40):12431-5.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nature Communications, 2016, 7(13182):1-9.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics," Trends Biotechnol., 28: 281-90, 2010.
Wheeler et al., "Microfluidic device for single-cell analysis," Analytical Chemistry, Jul. 2003, 75(14):3581-3586.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning," J Biomed Mater Res A., May 2008, 85(2):530-538.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yershov et al., "DNA analysis and diagnostics on oligonucleotide microchips," Proc. Natl. Acad. Sci. USA, May 1996, 93(10):4913-4918.
Yusof et al., "Inkjet-like printing of single-cells," Lab Chip, Jul. 2011, 11(14):2447-2454.
Zhang et al., "Block-Cell-Printing for live single-cell printing," PNAS, Feb. 2014, 111(8):2948-2953.
Zheng et al., "Massively parallel digital transcriptional profiling of single cells," Nat Commun., Jan. 16, 2017, 8:14049, 12 pages.
Zhu et al., "Reverse transcriptase template switching: a SMART approach for full-length cDNA library construction," Biotechniques, Apr. 2001, 30(4):892-897.
Marx, "Method of the Year: spatially resolved transcriptomics," Nature Methods, 2021, 18(1):9-14.
Vickovic et al., "Massive and parallel expression profiling using microarrayed single-cell sequencing," Nat. Commun. Oct. 14, 2016, 7:13182, 9 pages.

\* cited by examiner

SOLID STATE SINGLE CELL METHOD FOR ANALYZING FIXED BIOLOGICAL CELLS

CROSS-REFERENCE TO RELATED APPLICATIONS

This application claims priority or the benefit of U.S. Provisional Patent Application 62/982,495, filed Feb. 27, 2020, the contents of which are fully incorporated herein by reference.

FIELD

This invention relates to single-biological particle methods for analyzing fixed biological particles (e.g., cells or nuclei) using spatial transcriptomics.

BACKGROUND

Currently, techniques can be used to obtain information related to genomics, epigenomics, transcriptomics, proteomics and the like, for populations of cells on a single cell basis. In some examples, partitioning or drop-based microfluidic techniques may be used to encapsulate and manipulate single cells or nuclei.

Some cells may be difficult to analyze using these methods, however. Fixed cells, for example, may require decrosslinking steps that involve enzymes and/or detergents, which are harsh and may degrade cell integrity. Cells or nuclei treated in this way, for example, may leak analytes (e.g., mRNA), which analytes then are not localized to the partition or droplet that contains the cell and its analyte contents.

Methods and systems for performing single-cell analysis with fixed cells, which would accommodate harsh steps to reverse fixation, for example, are of interest.

SUMMARY

Disclosed are methods and systems for analyzing single biological particles (e.g., cells or nuclei) that maintain the single biological particles, such as cells or nuclei and their contents in a state of relative isolation during decrosslinking and subsequent hybridization, thereby preventing cellular analytes (e.g., mRNA, proteins, etc.) from diffusing away from the capture site of an individual biological particle (e.g., a cell or a nucleus). Limiting diffusion of analytes from one capture site (e.g., a cell capture site or region) toward other adjacent capture site (e.g., capture site or regions for other cells) provides advantages for downstream processing of the biological particles. As described herein, processing of analytes from a single biological particle (e.g., a cell or nucleus) at a single capture site using a set of nucleic acid barcode molecules having a common barcode sequence will provide a set of barcoded nucleic acid molecules comprising the common barcode sequence (or reverse complement thereof) and sequences corresponding to analytes from the single biological capture site. The common barcode sequence from one capture site can be used to distinguish the barcoded nucleic acid molecules of one biological particle from other common barcode sequences of other barcoded nucleic acid molecules of other biological particles captured on the substrate. The methods and systems retain single biological particles (e.g., cells or nuclei) on a surface or substrate using biological particle capture sites (or regions) (e.g., cell or nucleus capture sites (or regions)) that also have associated capture probes that capture analytes from the retained biological particles (e.g., cells or nuclei). Optionally, permeable polymer membranes over individual biological particles (e.g., cells or nuclei) retained on the surface that prevent analyte (e.g., mRNA, proteins, etc.) diffusion while permitting transmission of a decrosslinking agent to the biological particle (e.g., a cell or nucleus), followed by processing of cellular analytes from the individual biological particles by molecular barcoding and/or imaging of the analytes (e.g., cellular analytes).

In some examples, disclosed is a method of analysis for fixed single cells, comprising providing a substrate comprising a plurality of cell capture regions, wherein a cell capture region of the plurality of cell capture regions comprises a cell capture moiety and a plurality of barcode molecules, wherein the plurality of barcode molecules comprises a common barcode sequence and an analyte binding sequence; contacting a plurality of fixed single cells with the substrate to allow binding of the plurality of fixed single cells to the plurality of cell capture regions, thereby providing a captured fixed single cell at the cell capture region; reversing fixation of the captured fixed single cell to release a plurality of analytes from the captured fixed single cell, wherein diffusion of the plurality of analytes is substantially confined to the cell capture region; and generating a plurality of barcoded molecules from the plurality of analytes and the plurality of barcode molecules, wherein a barcoded molecule of the plurality of barcoded molecules comprises the common barcode sequence, or a complement thereof, and a sequence corresponding to the analyte. The method may further comprise applying a permeable coating to the substrate prior to reversing fixation, thereby immobilizing the captured fixed single cell. The method may further comprise providing a protein binding agent to the fixed single cell, wherein the protein binding agent is capable of specifically binding to a polypeptide from the fixed single cell.

Also disclosed is a system for analysis of fixed single cells, comprising a substrate including a plurality of cell capture regions, wherein a cell capture region includes a cell capture moiety and a plurality of barcode molecules, wherein a barcode molecule includes a common barcode sequence and an analyte binding sequence; an agent for reversing fixation in fixed single cells retained on the substrate; a permeable coating that can be applied to the substrate to immobilize single cells retained on the substrate; and reagents for generating barcoded molecules from cellular analytes captured by the analyte binding sequences.

Also disclosed are kits for analysis of fixed single cells.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

The following U.S. patents and U.S. published patent applications are each incorporated by reference in their entirety into this application:

U.S. Pat. No. 9,593,365 (Ser. No. 14/434,274), issued Mar. 14, 2017 and titled, "Methods And Product For Optimising Localized Or Spatial Detection Of Gene expression In A Tissue Sample";

U.S. Pat. No. 10,030,261 (Ser. No. 14/111,482), issued Jul. 24, 2018 and titled, "Method And Product For Localized Or Spatial Detection Of Nucleic Acid In A Tissue Sample";

U.S. Pat. No. 10,774,374 (Ser. No. 15/565,637), published Jul. 4, 2019 and titled, "Spatially Distinguished, Multiplex Nucleic Acid Analysis of Biological Specimens"; and U.S. Provisional Patent Application Ser. No. 63/033,348, filed Jun. 2, 2020 and titled, "Systems and Methods for Detecting Analytes from Captured Single Cells.

Other references incorporated by reference may be listed throughout the application.

BRIEF DESCRIPTION OF THE DRAWINGS

In the accompanying drawings, which are incorporated in and constitute a part of the specification, embodiments of the disclosed inventions are illustrated. It will be appreciated that the embodiments illustrated in the drawings are shown for purposes of illustration and not for limitation. It will be appreciated that changes, modifications and deviations from the embodiments illustrated in the drawings may be made without departing from the spirit and scope of the invention, as disclosed below.

DETAILED DESCRIPTION

Figure 1:
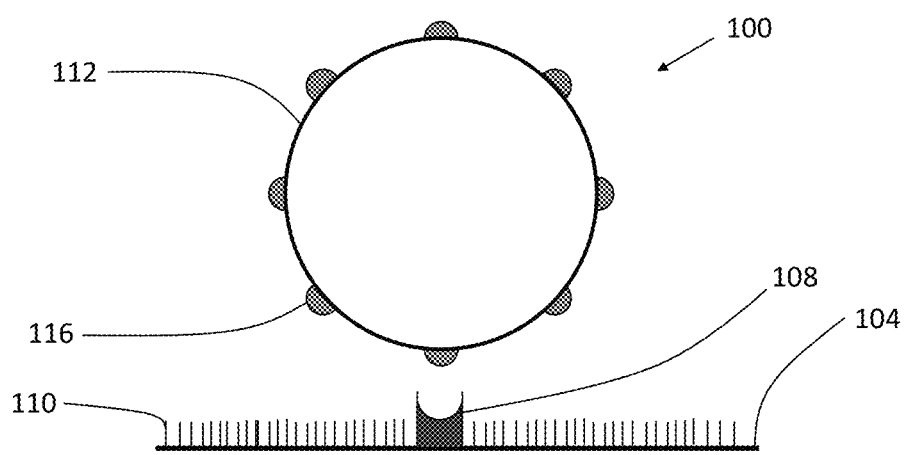
FIG. 1 is a schematic drawing (side view) that illustrates an example system of this disclosure.

Processing and analysis of fixed biological particles (e.g., cells or nuclei) in droplet-based partitioning systems can present challenges because treatment of the biological particles (e.g., cells or nuclei) prior to partitioning to reverse the fixation (e.g., decrosslinking, un-fixing) generally are needed. These treatments can be harsh, may cause analytes to leak from the biological particles, such as cells or nuclei, and to be lost prior to partitioning of biological particles into droplets and/or to be partitioned into droplets containing biological particles from which the analyte did not originate.

The present disclosure is directed to a method of analyzing single biological particles (e.g., cells or nuclei) that prevents or contains analyte (e.g., mRNA) leakage by immobilizing the single biological particles during decrosslinking and subsequent hybridization, and a system for analyzing the single biological particles.

The present disclosure concerns methods of analysis for fixed single biological particles (e.g., single cells or nuclei) and can be used for processing of single analytes (e.g., RNA, DNA, or protein) or multiple analytes simultaneously (e.g., DNA and RNA, DNA and protein, RNA and protein, or RNA, DNA and protein) (see WO/2019/157529, which is incorporated herein by reference in its entirety). In one embodiment, the analytes are intracellular analytes (e.g., nucleic acids such as mRNA and intracellular proteomic analytes such as peptides and polypeptides). The analytes may also be analytes expressed on the extracellular surface of a cell (e.g., an extracellular polypeptide or other molecule) (see US 2020-0002763 and WO/2019/157529, each of which is incorporated herein by reference in its entirety).

Definitions

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

Herein, "affinity" refers to attraction between objects. In some examples, affinity refers to the strength of a binding interaction between particles, like cells and individual molecules. In some examples, affinity may refer the ability of a cell capture site to retain a cell on a surface.

Herein, "amplification product" refers to molecules that result from reproduction or copying of another molecule. Generally, the molecules copied or reproduced are nucleic acid molecules, specifically DNA or RNA molecules. In some examples, the molecule reproduced or copied may be used as a template for the produced molecules. In some examples, an analyte captured by the capture domain of an oligonucleotide may be used as a template to produce an amplification product. In some examples, an mRNA captured by the capture domain of an oligonucleotide may be used as a template to produce a cDNA amplification product. Various enzymes (e.g., reverse transcriptase) may be used for this process. The cDNA amplification product may in turn act as a template for amplification that may also be called amplification products. Various enzymes (e.g., Taq polymerase) may be used for this process.

Herein, "analyte" refers to a substance whose chemical constituents are being identified and/or measured. Generally, this application refers to analytes from and/or produced by cells. Any or all molecules or substance from or produced by a cell may be referred to herein as analytes. Chemically, cellular analytes may include proteins, polypeptides, peptides, saccharides, polysaccharides, lipids, nucleic acids, and other biomolecules.

Herein, "array" refers to a region on a support that contains multiple demarcated regions of oligonucleotides, interspersed with intervening regions that do not contain oligonucleotides. In some examples, these regions may be referred to as "oligonucleotide arrays" or "capture areas". The arrays herein generally have oligonucleotides that contain spatial barcodes and, thus, the arrays may be referred to as "spatial" arrays.

Herein, "associated with" generally refers to barcode molecules that are in close proximity to a particular biological particle (e.g., cell or nucleus) capture moiety on a substrate. Generally, herein, barcode molecules associated with a particular biological particle capture moiety are distributed around that biological particle capture moiety such that analytes released from a biological particle captured by or bound to that biological particle capture moiety will contact the barcode molecules associated with that biological particle capture moiety and will not contact barcode molecules associated with other or adjacent biological particle capture moieties.

Herein, analytes released from biological particles (e.g., cells or nuclei) bound to biological particle capture moieties generally reach the associated barcode molecules by diffusion. A released analyte will have a better probability of contacting a barcode molecule, the closer the barcode molecule is located to the biological particles capture moiety which bound the biological particle.

Herein, "barcode," generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads. In some examples, a barcode may be a nucleotide sequence that is encoded by, linked to or associated with one or more oligonucleotides. In some examples, a specific barcode may correlate with a location of a barcode, on a support, for example. A barcode used to convey locational information may be called a spatial barcode.

Herein, "barcoded molecule" or, in some examples, "barcoded nucleic acid molecule" generally refers to a molecule or a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence (e.g., targeted by a primer sequence) or a non-targeted sequence. For example, in the methods, systems and kits described herein, hybridization and reverse transcription of the nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may be a nucleic acid product. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA as well as the sequence of the spatial barcode thereby determining the locational position of the mRNA along with its identity. Herein, molecules stated to have a "common barcode sequence" refers to molecules that are labeled or identified with the same barcode sequence.

Herein, "base-paired" generally refers to the situation where two complementary nucleic acids have formed hydrogen bonds between complementary nucleotides in the different strands. Two such nucleic acid strands may be referred to as hybridized to one another.

Herein, "bind" generally refers to a stable physical interaction between substances. For example, cells may bind to other cells. Cells may bind to molecules. Molecules may bind to cells. Molecules may bind to other molecules. In some examples, binding of substances may be specific. "Binding" refers to causing substances to bind.

The term "biological particle," as used herein, generally refers to a discrete biological system derived from a biological sample. The biological particle may be a macromolecule, small molecule, virus, cell, cell derivative, cell nucleus, cell organelle, cell constituent and the like. Examples of a cell organelle include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological particle may contain multiple individual components, such as macromolecules, small molecules, viruses, cells, cell derivatives, cell nuclei, cell organelles and cell constituents, including combinations of different of these and other components. The biological particle may be or may include DNA, RNA, organelles, proteins, or any combination thereof. These components may be extracellular. In some examples, the biological particle may be referred to as a clump or aggregate of combinations of components. In some instances, the biological particle may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when comprising a gel or polymer matrix.

Herein, "capable" means having the ability or quality to do something.

Herein, "capture" generally refers to the capability of a first substance to interact with and/or bind a second substance where, for example, the second substance is part of a population of other substances. An analyte may be captured. In some examples, capture refers to identification of a target nucleic acid molecule (e.g., an RNA) by its hybridization to a capture probe, and/or amplification of a target nucleic acid molecule or a nucleic acid probe hybridized to it (e.g., an RNA or a probe hybridized to the RNA) using, for example polymerase chain reaction (PCR) and/or nucleic acid extension of a target nucleic acid molecule or a capture probe hybridized to it using, for example reverse transcription reactions.

Herein, "capture probe" refers to a molecule (e.g., an oligonucleotide) that contains a capture domain.

Herein, "capture domain" or "analyte binding site" means a part of a molecule that is capable of binding or capturing a substance. An analyte capture domain may be capable of capturing analytes that may include proteins, polypeptides, peptides, saccharides, polysaccharides, lipids, nucleic acids, and other biomolecules. In some examples, the analyte capture domain may be a nucleotide sequence capable of hybridizing to an analyte that contains a complementary nucleotide sequence. Herein, "nucleotide capture sequence" refers to a first nucleotide sequence that is capable of capturing (e.g., by hybridizing to) a second nucleotide sequence. In some examples, an analyte capture domain may contain modified nucleotides.

Herein, "biological capture moiety" or "biological capture site" refers to a location on a substrate to which a biological particle may bind. A "cell capture moiety" or "cell capture site" refers to a location on a substrate to which a cell may bind. A "nucleus capture moiety" or "nucleus capture site" refers to a location on a substrate to which a nucleus may bind. Generally, a capture moiety may have or contain substances to which a biological particle (e.g., a cell or nucleus) may bind. The biological particle binding to the substances may be specific binding. In some examples, the substances may be molecules to which certain biological particles (e.g., cells or nuclei) may specifically bind. In some examples, the substances may be specific ligands or cognate ligands for receptors on a biological particle.

Herein, "cell capture region" refers to a region on a substrate that contains a cell capture moiety and a plurality of barcode molecules associated with the cell capture moiety. A "nucleus capture region" refers to a region on a substrate that contains a nucleus capture moiety and a plurality of barcode molecules associated with the nucleus capture moiety. A "biological particle capture region" refers to a region on a substrate that contains a biological particle capture moiety and a plurality of barcode molecules associated with the biological particle capture moiety.

Herein, "coat" or "coating" refers to a polymer layering covering biological particles (e.g., cells or nuclei) attached to biological particle capture moieties.

Herein, "complementary," in the context of one sequence of nucleic acids being complementary to another sequence, refers to the ability of two strands of single-stranded nucleic acids to form hydrogen bonds between the two strands, along their length. A complementary strand of nucleic acids is generally made using another nucleic acid strand as a template. A first nucleotide that is capable of hybridizing to a second nucleotide sequence may be said to be a complement of the second nucleotide sequence.

Herein, "configured to" generally refers to a component of a system that can perform a certain function.

Herein, "contact" refers to physical touching of separate substances or objects. "Contacting" refers to causing separate substances to physically touch one another.

Herein, "crosslinking," means connecting or attaching two or more separate substances to each other. The connecting or attaching is due to formation of crosslinks. In some examples, crosslinking refers to formation of chemical bonds between two or more atoms in a molecule or in different molecules.

Herein, "diffusion" means to spread over an area. Generally, herein, analytes diffuse from a biological particle (e.g., a cell or nucleus) to contact barcode molecules associated with a biological particle capture moiety. In some examples, analytes from one biological particle may diffuse to contact barcode molecules associated with another biological particle.

Herein, "fix," refers to formation of covalent bonds, such as crosslinks, between biomolecules or within molecules. The process of fixing biological particles (e.g., cells or nuclei) for example, is called "fixation." The agent that causes fixation is generally referred to as a "fixative" or "fixing agent." Fixed "biological particles" (e.g., fixed cells or nuclei) or "fixed tissues" refers to biological particles or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. Non limiting examples of fixatives or fixing agents include methanol, paraformaldehyde, formalin, and acetone to name a few. Other fixing agents may include alcohol, ketone, aldehyde, cross-linking agents, disuccinimidyl suberate (DSS), dimethylsuberimidate (DMS), formalin, dimethyladipimidate (DMA), dithio-bis(-succinimidyl propionate) (DSP), disuccinimidyl tartrate (DST), ethylene glycol bis (succinimidyl succinate) (EGS), bis-imidazole-carboxylate compounds, and combinations thereof.

Herein, "flow" refers to a moving liquid. "Flowing" refers to causing a liquid to flow. Generally, herein, flowing refers to causing a liquid containing biological particles (e.g., cells or nuclei) to contact biological particle capture moieties.

Herein, "hybridize" refers to a nucleotide sequence of a single-stranded nucleic acid molecule forming a complex with a nucleic acid molecule having a complementary nucleotide sequence. Generally, the complex forms through hydrogen bonding between complementary nucleotide bases in separate nucleic acid molecules.

Herein, "hybridizing nucleotide sequence" refers to a nucleotide sequence, within an oligonucleotide for example, that is capable of hybridizing with a complementary nucleotide sequence in a target nucleic acid molecule present on or within a biological particle (e.g., a cell or nucleus) from a tissue sample (e.g., cellular RNA). When a hybridizing nucleotide sequence is of such a length that it hybridizes with a complementary, either fully or partially, nucleotide sequence that is unique to a target nucleic acid molecule(s) (e.g., cellular RNA or family of RNAs), the hybridizing nucleotide sequence may be said to hybridize to the same target nucleic acid molecule (e.g., the same RNA)

Herein, "immobilize" means to restrict or prevent movement.

Herein, "intervening region" or "interspot space" refers to areas on a support of an array that do not contain attached oligonucleotides.

Herein, "labeling agent" refers to molecules, substances and the like, that can be used to label or tag biological particles (e.g., cells or nuclei), and can be bound by biological particle capture moieties to retain biological particles on a support.

Herein, "library" refers to a collection of molecules having nucleotide sequences that are generally representative (e.g., comprising the same nucleotide sequences or complementary nucleotide sequences) of nucleotide sequences present in the molecules from the target nucleic acids. Generally, the molecules from which a library is made act as templates for synthesis of the collection of molecules that make up the library. The "library" may be, or may be produced from, amplification products of the target nucleic acid. Herein, libraries can be created from amplification of a mRNA analyte, or copies thereof, captured on an array. Therefore, the library can be derived from the captured target nucleic acid.

Herein, "oligonucleotide" means a linear polymer of nucleotides, in some examples 2'-deoxyribonucleotides. Oligonucleotides are single stranded. Oligonucleotides can be of various lengths. Oligonucleotides can include modified nucleotides as known in the art.

Herein, "partition" generally, refers to a space or volume that may be suitable to contain one or more species or conduct one or more reactions or processes. A partition may be a physical compartment, such as a droplet or well (e.g., a microwell). The partition may isolate space or volume from another space or volume, such as regions between capture regions on an array where there are typically no capture oligonucleotides. Herein, regions on an array where there are typically no capture oligonucleotides may also be referred to as intervening regions.

Herein, "permeable" refers to something that allows certain materials to pass through it.

Herein, "planar" refers to the shape of a plane (e.g., flat).

Herein, "polymer," refers to a substance having a large number of repeating units.

Herein, "primer" means a single-stranded nucleic acid sequence that provides a starting point for DNA synthesis. Generally, a primer has a nucleotide sequence that is complementary to a template, and has an available 3'-hydroxyl group to which a transcriptase or polymerase can add additional nucleotides complementary to corresponding nucleotides in the template, to synthesize a nucleic acid strand in the 3' to 5' direction.

Herein, "provide" means to make available. Providing is the act of making something available.

Herein, "retain" generally refers to a biological particle (e.g., a cell or nucleus) bound to a biological particle capture moiety and being immobilized there. "Retaining in place" may refer to this state of a biological particle on a substrate.

Herein, "RNA capturing probe" refers to a nucleic acid molecule capable of hybridizing to an RNA.

Herein, "select" generally refers to obtaining specific biological particles (e.g., cells or nuclei) from a population of biological particles. In some examples, subpopulations of biological particles (e.g., cells or nuclei) may be obtained or selected from a biological particle population.

Herein, "spatial" refers to a location within or on a space. In some examples, the space may be a two-dimensional space.

Herein, "support," when used as a noun, refers to something that serves, for example, as a foundation for another thing. In some examples, the support may be larger, more easily worked with, or more easily tracked or visualized than the thing being supported. A support may be a solid support. In some instances, a support may be dissolvable, disruptable, and/or degradable. In some cases, a support may not be degradable. A support may comprise a glass, plastic, metal, and/or other substances. In some cases, the support can be rigid. In other cases, the support may be flexible and/or compressible. In some examples, a support may be referred to as a "substrate."

Herein, "surface" means the outside part or upper layer of something. Herein, a "surface" of an array generally refers to a surface of a support or substrate that has oligonucleotides attached.

Herein, "template" refers to one single-stranded nucleic acid acting as a "template" for synthesis of another complementary single-stranded nucleic acid. For example, RNA can act as a template for synthesis of a complementary DNA strand synthesized using reverse transcriptase. A single-stranded DNA can act as a template for synthesis of a complementary DNA strand, most often by a DNA polymerase.

Herein, "un-fixed" or "decrosslink" refers to the processed condition of a biological particle (e.g., a cell or nucleus), a plurality of biological particles (e.g., cells or nuclei), a tissue sample or any other biological sample that is characterized by a prior state of fixation followed by a reversal of the prior state of fixation. For instance, an un-fixed biological particle may also be referred to as a "previously fixed" biological particle. In one embodiment, an un-fixed cell is characterized by broken or reversed covalent bonds in the biomolecules of the biological particle(s) (e.g., cell(s) or nucleus(ei)) or sample, where such covalent bonds were previously formed by treatment with a fixation agent (e.g., paraformaldehyde or PFA). In some examples, unfixing may be facilitated by particular fixing agents used to fix biological particles. In some examples, the chemical reactions that result from functioning of certain fixing agents may be reversed in absence of conventional un-fixing or decrosslinking agents. In some examples, certain bis-imidazole-carboxylate compounds may be used to prepare reversibly fixed biological samples, as described in PCT application no. PCT/US2020/066705, filed Dec. 22, 2020 and claiming priority to Dec. 23, 2019.

Herein, "unique molecular identifier" or "UMI" generally refers to an identifier of a particular analyte captured by a capture probe.

Capture Regions with Cell Capture Moieties and Barcoded Oligonucleotides

The methods described here use systems for capturing single biological particles (e.g., cells or nuclei), generally fixed biological particles (e.g., fixed cells or fixed nuclei). The captured biological particles are un-fixed (e.g., fixation of the biological particles is reversed), analytes from the biological particles are captured, and the captured analytes are analyzed, generally to provide information on presence and/or amounts of specific analytes within the captured biological particles.

Example systems of this application generally have at least three components: a substrate, a biological particle (e.g., cell or nucleus) capture moiety attached to the substrate and a plurality of barcode molecules associated with the biological particle capture moiety. In some examples, a biological particle capture moiety and the plurality of barcode molecules associated with it may be called a biological particle capture region. Generally, the substrates of this application contain multiple biological particle capture regions.

The fixed single biological particles (e.g., cells or nuclei) can be captured on a surface or substrate having a plurality of barcoded spots or cell capture regions. Each biological particle capture region has an individual biological particle capture site or biological particle capture moiety that is designed for capture of one fixed biological particle. The biological particle capture regions also have barcoded oligonucleotides that contain capture domains that bind analytes. The biological particle capture regions can be positioned at spaced intervals on any surface that is suitable for molecular barcoding and/or imaging and can be positioned at spaced intervals on a suitably primed surface of a substrate (e.g., a slide configured for reverse transcription of mRNA) used for molecular barcoding and/or imaging in spatial analysis. Various examples of the systems of this disclosure and their components are set forth in the following paragraphs and referenced figures.

In some examples, the substrate may be planar or substantially planar. In some examples, the shape of the substrate may be similar to that of a microscope slide or cover slip. Example substrates may flat and may lack microwells. Generally, the substrate is solid and example substrates may be glass or plastic. In some examples, the substrate is transparent to light. The substrates may be of various sizes and thicknesses. Dimensions of the substrates may be dictated by any instruments used to perform the methods disclosed in the application. The substrates may be configured to accept or attach biological particle (e.g., cell or nucleus) capture moieties and/or components thereof. The substrates may be configured to accept or attach barcode molecules. In some examples, the substrates and/or surfaces thereof, may be coated or modified to accept the biological particle capture moieties and/or barcode molecules. In some examples, biological particle capture moieties and/or barcode molecules may be printed onto a substrate.

FIG. 1 is a schematic drawing (side view) that illustrates an example system 100 of this disclosure. The drawing shows a substrate 104 that contains a biological particle (e.g., a cell or nucleus) capture moiety 108. A biological particle 112 may have a molecule or substance 116, sometimes a "labeling agent," that is able to bind to the biological particle capture moiety 108, resulting in retention of the biological particle 112 on the substrate 104. Multiple barcode molecules 110 are attached to the substrate 104. Generally, herein, a biological particle capture moiety 108 in combination with barcode molecules 110 associated with that biological particle capture moiety 108 can be referred to as a biological particle capture region.

Figure 2:
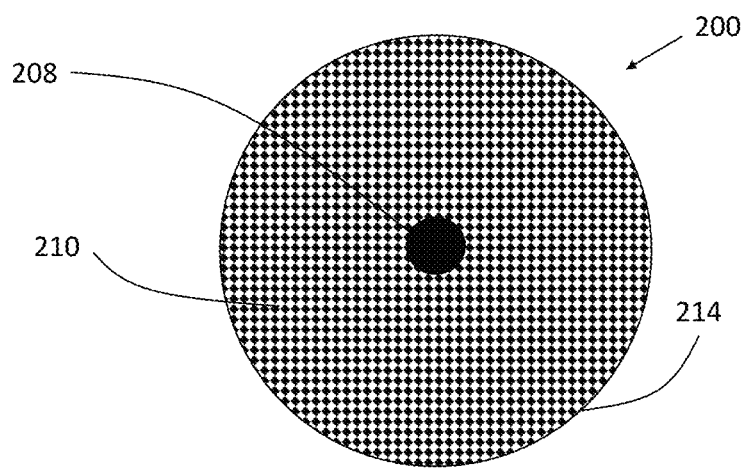
FIG. 2 is a schematic drawing (top view) that illustrates an example of a cell capture region of this disclosure.

FIG. 2 is a schematic drawing (top view) that illustrates an example of a biological particle (e.g., a cell or nucleus) capture region 200 of this disclosure. Such a region, that contains an uninterrupted area of oligonucleotides attached to a support, may be referred to as a "demarcated region" 214. The biological particle capture region 200 contains a biological particle capture moiety 208 and a plurality of barcode molecules 210, the barcode molecules 210 of the type shown in FIGS. 3 and 4, below. In the example, each dot 210 within the demarcated region 214 represents one or more oligonucleotides attached to the support. In some examples, the oligonucleotides 210 within the demarcated region 214 may all contain the same barcode sequence that corresponds to the location on the support where the oligonucleotides 210 are attached (e.g., spatial barcode). In some examples, the oligonucleotides 210 may have analyte capture domains that may be poly(dT). In some examples, the oligonucleotides 210 within the demarcated region 214 may contain different unique molecular identifiers. In some examples, the oligonucleotides 210 within the demarcated region 214 may contain different barcode sequences that correspond to the analyte capture domain encoded by the oligonucleotide (e.g., the oligonucleotides within the demarcated region 214 may have different analyte capture domains). In some examples, the oligonucleotides 210 within the demarcated region 214 may be said to represent a species of oligonucleotides. In some examples, a species of oligonucleotides 210 may be oligonucleotides 210 with at least one barcode nucleotide sequence in common. In some examples, the barcode sequence in common may be a barcode sequence corresponding to a location on a support to which the oligonucleotides 210 are attached (e.g., spatial barcode). As described below, a support may contain multiple, adjacent demarcated regions 214. In some examples, the oligonucleotides 210 of a region may all have the same spatial barcode. In some examples, the oligonucleotides of different regions may have different spatial barcodes.

Referring to FIG. 2, in some examples, the biological particle (e.g., cell or nucleus) capture moiety 208 can contain substances or molecules that can bind biological particles (e.g., cells or nuclei), thus retaining biological particles on a surface of a substrate. In some examples, such substances that are part of or contained within a biological particle capture moiety can bind specific biological particles (e.g., in the case of cells, antibodies binding a cellular antigen; a receptor molecule binding a ligand for the receptor). In some examples, such substances may bind biological particles nonspecifically (e.g., in the case of cells, bind any cell). In some examples, a biological particle capture moiety 208 can contain a substance configured to interact with a labeling agent that is used to label biological particles.

Figure 3:
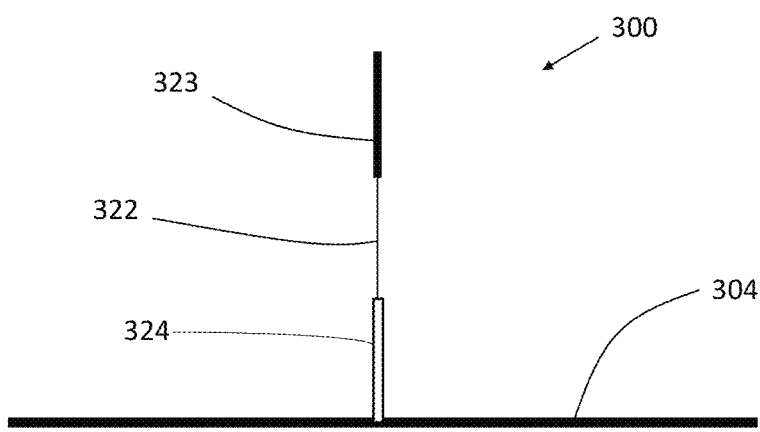
FIG. 3 is a schematic drawing (side view) illustrating an example of a spatial array oligonucleotide capture probe.

FIG. 3 is a schematic drawing (side view) that illustrates an example of a barcoded oligonucleotide 300. The oligonucleotide 300 is shown attached to a support or substrate 304. The barcode molecule 300 may have a variety of regions. One example region is an analyte capture domain 323. Another example region is a barcode nucleotide sequence 322. The barcode sequence 322 may be common to a plurality of the oligonucleotides 300. A barcode sequence 322 may correspond to a location on the support 304 where the oligonucleotide 300 is attached or immobilized (e.g., spatial barcode). A unique molecular identifier (UMI) may also be included as part of the barcoded oligonucleotide 300. A UMI sequence may correspond to a unique molecular identifier (UMI) associated with the oligonucleotide 300. The oligonucleotide 300 may have multiple barcode sequences 322. In some examples, an oligonucleotide 300 may have a barcode sequence that corresponds to the oligonucleotide 300 and a barcode sequence that corresponds to the location on the support 304 where the oligonucleotide is attached. The oligonucleotide may have other or additional regions 324 (e.g., PCR handles, cleavage domains, sequencing primer domains, etc.).

Figure 4:
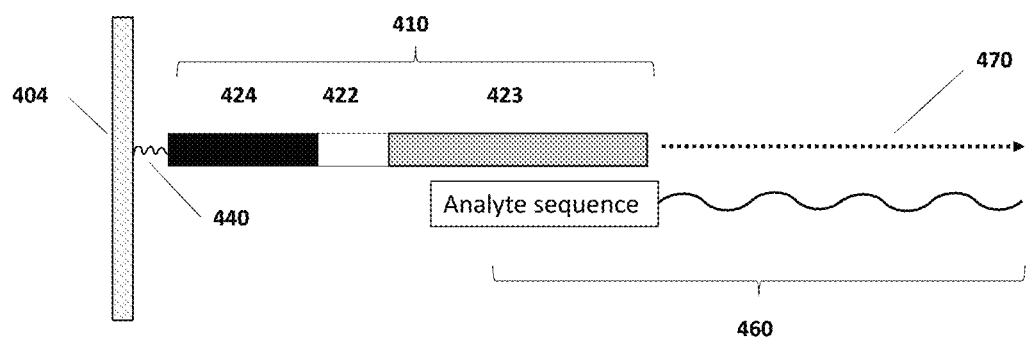
FIG. 4 is a schematic drawing (side view) that illustrates an example of a capture probe attached to a support.

In FIG. 4, a nucleic acid barcode molecule 410 comprises a sequence 423 complementary to a sequence of an RNA molecule 460 from a biological particle (e.g., a cell or nucleus). In some instances, sequence 423 comprises a sequence specific for an RNA molecule. In some instances, sequence 423 comprises a poly-T sequence. In some instances, sequence 423 comprises a sequence complementary to a region of mRNAs encoding specific proteins. Sequence 423 is hybridized to RNA molecule 460 and extended via a nucleic acid reaction (e.g., a cDNA molecule 470 is generated in a reverse transcription reaction) generating a barcoded nucleic acid molecule comprising a capture region (e.g., capture region specific) barcode sequence 422 (or a reverse complement thereof) and a sequence of the extended nucleic acid (e.g., cDNA 470) (or a portion thereof). Barcoded nucleic acid molecules can then be optionally processed to amplify the molecules and/or append sequencing platform specific sequences to the fragments. See, e.g., U.S. Pat. Pub. No. 2018/0105808 (Ser. No. 15/825, 740) which is hereby incorporated by reference in its entirety. Barcoded nucleic acid molecules, or derivatives generated therefrom, can then be sequenced on a suitable sequencing platform. Nucleic acid barcode molecule 410 may be attached to support or substrate 404 optionally via a releasable linkage 440 (e.g., comprising a labile bond), such as those described U.S. Pat. Pub. No. 2020/0063191 (Ser. No. 16/680,343), as well as WO2020/047007A2 (Appl. No. PCT/US2019/048430), WO2020/047010A2 (Appl. No. PCT/US2019/048434), WO2020/047004A3 (Appl. No. PCT/US2019/048427), and WO2020/047005A1 (PCT/US2019/048428), each of which are each incorporated by reference herein in their entirety.

Figure 5:
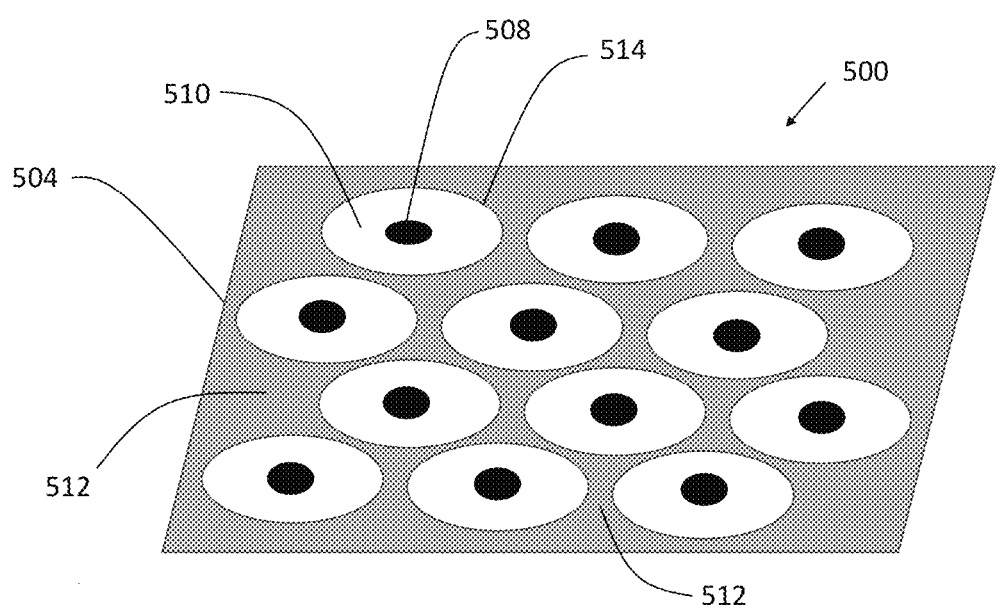
FIG. 5 is a schematic drawing (top, angular view) that illustrates an example of a region on a support with multiple species of capture probes (e.g., a spatial array).

FIG. 5 is a schematic drawing (top, angular view) that illustrates an example system of this disclosure 500 that contains multiple regions that demarcate individual biological particle (e.g., cell or nucleus) capture regions 514. In the drawing, the substrate 504 has multiple (12 are shown) biological particle capture regions 514 on its surface. Between individual biological particle capture regions 514 are intervening regions 512. Some example systems 500 may not have intervening regions 514 and, thus, may have continuous uninterrupted areas of barcoded oligonucleotides 510 attached to the support 504. Each biological particle capture region has a biological particle capture moiety 508 and a plurality of barcode molecules 510, examples of barcode molecules which are shown in FIGS. 3 and 4, associated with the biological particle capture moiety.

Referring to FIG. 5, in some examples, the biological particle capture regions 514 can have diameters of about 5 to about 500 microns, 15 to about 150 microns, or about 30 to about 80 microns. The single biological particle capture moieties 508 can have diameters that are smaller than the diameters of the corresponding biological particle capture regions 514. For example, the biological particle capture moieties 508 can have diameters of about 0.5 to about 100 microns, or about 1 to about 15 microns, or about 5 to about. The preferred diameters can vary widely depending on the size and type of the single biological particles (e.g., cells or nuclei) being captured.

A single biological particle capture moiety 508 is applied to a portion of each biological particle capture region 514, suitably in a central region of each biological particle capture region 514 and has a diameter smaller than the diameter of the corresponding biological particle capture region 514. For example, the diameter of the single biological particle capture moiety 508 can be from about 1% to about 50% of the diameter of the corresponding biological particle capture region 514, suitably about 2% to about 25%, or about 5% to about 15% of the diameter of the barcoded spot. Each single biological particle capture moiety 508 can have a diameter that enables the capture of only one single biological particle and can have a diameter that approximates the diameter of the single biological particle being analyzed.

Each single biological particle capture moiety 508 has a chemistry (described below) that enables it to capture and hold a single biological particle in place, thereby immobilizing it during decrosslinking and subsequent processing (e.g., nucleic acid hybridization). Each single biological particle capture moiety 508 and surrounding biological particle capture region 514 can include a suitable nucleic acid primer (e.g., a reverse transcription primer as described below) designed to hybridize nucleic acids (e.g., mRNA) from the captured single biological particle. Each single biological particle capture moiety 508 and, optionally, each surrounding biological particle capture region 514 can be coated with a permeable polymer membrane (described below) to immobilize the single biological particle and its contents, to maintain any dissociated nucleic acid (e.g., mRNA) within the vicinity of the single biological particle capture site, and to prevent any dissociated nucleic acid (e.g., mRNA) from diffusing to adjacent biological particles. While most of the nucleic acid molecules (e.g., mRNA) will be contained within the single biological particle capture moiety 508, any nucleic acid molecules (e.g., mRNA) that diffuse from the capture site can be hybridized to oligonucleotides 510 that are part of the biological particle capture region 514 instead of migrating to neighboring biological particles and capture sites. The chemistries of the biological particle capture regions 514 and the biological particle capture moieties 508 are described below.

Barcoded Oligonucleotides of Biological Particle Capture Regions

Example barcode molecules disclosed in this application may have one or more barcodes. Example barcode molecules may have one or more analyte binding sequences. In some examples, a plurality of barcode molecules may be associated with one or more biological particle (e.g., cell or nucleus) capture moieties. The combination of the one or more biological particle capture moieties and the barcode molecules associated with the biological particle capture moieties may be referred to as a biological particle capture region. In some examples, barcode molecules associated with one or more biological particle capture moieties, and that make up a single biological particle capture region, are arranged such that analytes released from biological particles that bind the biological particle capture moiety or moieties of the biological particle capture region diffuse from the biological particles such that they contact the barcode molecules associated with the particular biological particle capture moiety or moieties of the biological particle capture region, and do not diffuse such that they contact barcode molecules associated with other biological particle capture regions. In some examples, a biological particle capture region may contain about $10^3$, $10^4$, $10^5$, $10^6$, $10^7$, $10^8$ or $10^9$ barcode molecules associated with the biological particle capture moiety or moieties of the biological particle capture region. In some examples, a biological particle capture region may be between about 10 and $10^3$ μm across, or between about 10 and $10^3$ μm from a first border or edge to a second border or edge directly across from the first. In some examples, the plurality of barcode molecules associated with a particular biological particle capture moiety or moieties, or that are part of a single biological particle capture region, are within about 10 to $10^6$ μm of each other. In some examples, a distance between adjacent biological particle capture regions may be between about 1 and $10^2$ μm. In some examples, a substrate may contain between about $10^3$ and $10^8$ capture regions. In some examples, a polymer coating may be applied to the substrate after biological particle capture, such that analytes released from biological particles bound by one biological particle capture region are unable to diffuse to a second biological particle capture region.

Analyte binding sequences (i.e., capture domains) of barcode molecules may be configured to bind analytes from a biological particle (e.g., a cell or nucleus). Analyte binding sequences may be configured to bind specific analytes from a biological particle, such that analytes that a particular analyte binding sequence is not configured to bind are not bound. Analyte binding sequences may be designed to bind any type of molecule. For example, analyte binding sequences may be designed to bind proteins, polysaccharides, lipids, nucleic acids, and the like.

The systems disclosed in this application may be used to detect many different types of analytes. Cellular analytes that are suitable for use with the systems of this disclosure include, without limitation, intracellular and extracellular analytes. The cellular analyte may be a protein, a metabolite, a metabolic byproduct, an antibody or antibody fragment, an enzyme, an antigen, a carbohydrate, a lipid, a macromolecule, or a combination thereof (e.g., proteoglycan) or other biomolecules. The cellular analyte may be a nucleic acid molecule. The cellular analyte may be a deoxyribonucleic acid (DNA) molecule or a ribonucleic acid (RNA) molecule. The DNA molecule may be a genomic DNA molecule. The cellular analyte may comprise coding or non-coding RNA. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA.

In some instances, the cellular analyte is associated with an intermediary entity, wherein the intermediary entity is analyzed to provide information about the cellular analyte and/or the intermediary entity itself. For instance, an intermediary entity (e.g., an antibody) may be bound to an extracellular analyte (e.g., a cell surface receptor), where the intermediary entity is processed to provide information about the intermediary entity, the extracellular analyte, or both. In one embodiment, the intermediary entity comprises an identifier (e.g., a barcode).

In some examples, analyte binding sequences contain nucleotide sequences that can capture other, complementary nucleotide sequences, through hybridization. In some examples, the complementary nucleotide sequences are part of an analyte from a cell that includes DNA, RNA, mRNA, sequences that are complementary to sequences in the DNA, RNA or mRNA, or amplification products from the DNA, RNA or mRNA or their complementary sequences.

Referring to FIG. 5, the barcoded oligonucleotides 510 of the biological particle (e.g., cell or nucleus) capture regions 514 can be designed to perform at least two functions, labelling and hybridization. The at least two functions can be performed by using a single barcoded primer (e.g., a reverse transcription primer), which facilitates hybridization and comprises a barcode (e.g., a nucleic acid barcode sequence), or by using separate barcoding (labeling) and a primer (e.g., a reverse transcription primer for hybridization) materials. In other words, for instance the biological particle capture regions 514 can include a barcoded reverse transcription primer, or some combination of a reverse transcription primer and a barcode material (e.g., a nucleic acid barcode sequence).

The barcoded oligonucleotides 510 of the biological particle capture regions 514 can be formed using any suitable barcode material (e.g., nucleic acid barcode molecules) that can be printed or otherwise formed as barcodes in the demarcated regions 514 on the surface of the substrate 504. The barcodes can be a label or other identifier that conveys or is capable of conveying information, e.g., information about the mRNA in the single biological particles (e.g., single cells or nuclei) being analyzed. The barcodes can have a variety of different chemistries. For example, the barcodes can include polynucleotide barcodes, random nucleic acid and/or amino acid sequences, synthetic nucleic acid and/or amino acid sequences, or any combination of the foregoing. The barcodes can allow for identification and/or quantification of individual sequencing-reads, e.g., a barcode can be or can include a unique molecular identifier or "UMI." In some embodiments, a barcode can include two or more sub-barcodes that together function as a single barcode. For example, a polynucleotide barcode can include two or more polynucleotide sequences or sub-barcodes that are separated by one or more non-barcode sequences. A barcode can be a fluorescent barcode to which fluorescently labeled oligonucleotides hybridize. A barcode can be attached to an mRNA molecule or other oligonucleotide.

The barcode sequences can include from about 6 to about 20 or more nucleotides. In some embodiments, the length of a barcode sequence can be about 6, 7, 8, 9, 10, 11, 12, 13, 14, 15, 16, 17, 18, 19, 20 nucleotides or longer. In some embodiments, the length of a barcode sequence is at most about 6, 7, 8, 9, 10, 11, 12, 13, 14, 15, 16, 17, 18, 19, 20 nucleotides or shorter. The nucleotides can be completely contiguous, e.g., in a single stretch of adjacent nucleotides, or they can be separated into two or more subsequences that are separated by one or more nucleotides. Separated spatial barcode subsequences can be from about 4 to about 16 nucleotides in length. In some embodiments, the separated barcode subsequence can be about 4, 5, 6, 7, 8, 9, 10, 11, 12, 13, 14, 15, 16 nucleotides or longer. In some embodiments, the separated barcode subsequence can be at most about 4, 5, 6, 7, 8, 9, 10, 11, 12, 13, 14, 15, 16 nucleotides or shorter.

The barcoded oligonucleotides 510 of the biological particle capture regions 514 can include a nucleic acid primer (e.g., a reverse transcription primer) that includes a functional nucleic acid sequence (herein "oligonucleotide domain") configured to interact with the target analyte (e.g., mRNA molecules) in the single biological particle being analyzed, and to hybridize to the target analyte for further processing (e.g., reverse transcription of an mRNA target analyte to yield cDNA. The primer (e.g., a reverse transcription primer) can be barcoded to include all or a portion of the foregoing barcode materials, can be chemically attached to the barcodes, or can be applied to the barcoded spots separate from the barcode materials.

In one embodiment, the functional nucleic acid sequence of the reverse transcription primer can include a poly(T) sequence that is configured to interact with the mRNA molecules via the poly(A) tail of an mRNA transcript. In the present invention, any such primer (e.g., the reverse transcription primer) can include capture domains (referred to herein as "oligonucleotide domains") such as ribonucleotides and/or deoxyribonucleotides as well as synthetic nucleotide residues that can participate in Watson-Crick type or analogous base pair interactions with the target mRNA. The oligonucleotide domains can prime a reverse transcription reaction to generate cDNA that is complementary to the target mRNA molecules. The oligonucleotide domains can be ligated to one strand of the target mRNA molecules. For example, SplintR ligase along with RNA or DNA sequences (e.g., degenerate RNA) can be used to ligate a single-stranded mRNA to an oligonucleotide domain. In some embodiments, ligases with RNA-templated ligase activity, e.g., SplintR ligase, T4 RNA ligase 2 or KOD ligase, can be used to ligate a single-stranded mRNA to the oligonucleotide domain.

In some embodiments, an oligonucleotide domain of the reverse transcription primer includes a splint oligonucleotide. An oligonucleotide domain can include a free 3' end that can be extended, e.g., by template dependent polymerization, to form an extended oligonucleotide domain. The oligonucleotide domain can be selected or designed to bind selectively or specifically to a target mRNA by way of hybridization to the mRNA poly(A) tail. Thus, the oligonucleotide domain can include a poly(T) DNA oligonucleotide, e.g., a series of consecutive deoxythymidine residues linked by phosphodiester bonds, which is capable of hybridizing to the poly(A) tail of mRNA. The oligonucleotide domain can include oligonucleotides that are functionally or structurally analogous to a poly(T) tail, for example, a poly(U) oligonucleotide or an oligonucleotide including deoxythymidine analogues. The oligonucleotide domain can have any sequence that is capable of binding to mRNA. In some embodiments, a homopolymer sequence is added to an mRNA molecule using a terminal transferase enzyme in order to produce a molecule having a poly(A) or poly(T) sequence. For example, a poly(A) sequence can be added to an mRNA, thereby making the mRNA capable of capture by a poly(T) oligonucleotide domain.

In some embodiments, random sequences, e.g., random hexamers or similar sequences, can be used to form all or a part of the oligonucleotide domain. For example, random sequences can be used in conjunction with poly(T) (or poly(T) analogue) sequences. Thus, when the oligonucleotide domain includes a poly(T) (or a "poly(T)-like") oligonucleotide, it can also include a random oligonucleotide sequence (e.g., "poly(T)-random sequence" probe). This can, for example, be located at 5' or 3' of the poly(T) sequence, e.g., at the 3' end of the oligonucleotide domain.

The poly(T)-random sequence can facilitate the capture of the mRNA poly(A) tail. In some embodiments, the oligonucleotide domain can be an entirely random sequence. In some embodiments, degenerate oligonucleotide domains can be used.

In some embodiments, a pool of two or more oligonucleotide domains form a mixture, where one oligonucleotide domain includes a poly(T) sequence and another oligonucleotide domain includes random sequences. In some embodiments, a pool of two or more oligonucleotide domains form a mixture where the one oligonucleotide domain includes a poly(T)-like sequence and another oligonucleotide domain includes random sequences. In some embodiments, a pool of two or more oligonucleotide domains form a mixture where one oligonucleotide domain includes a poly(T)-random sequences and another oligonucleotide domain includes random sequences. In some embodiments, degenerate oligonucleotide domains can be added to any of the preceding combinations listed herein. In some embodiments, degenerate oligonucleotide domains can be substituted for one of the oligonucleotide domains in each of the pairs described herein.

The oligonucleotide domain of the reverse transcription primer can be based on a gene sequence, a motif sequence or common/conserved sequence that it is designed to capture (i.e., a sequence-specific oligonucleotide domain). Thus, the oligonucleotide domain can be capable of binding selectively to a desired sub-type or subset of nucleic acid, for example a type or subset of mRNA. In some embodiments, the oligonucleotide domain includes an "anchor" or "anchoring sequence," which is a sequence of nucleotides designed to ensure that the oligonucleotide domain captures and hybridizes to the intended mRNA. The anchor sequence can include a sequence of nucleotides, including a 1-mer, 2-mer, 3-mer or longer sequence. The sequence can be random. For example, an oligonucleotide domain including a poly(T) sequence can be designed to capture an mRNA. An anchoring sequence can include a random 3-mer (e.g., GGG) that helps ensure that the poly(T) oligonucleotide domain hybridizes the mRNA. In some embodiments, an anchoring sequence can be VN, N, or NN. Alternatively, the sequence can be designed using a specific sequence of nucleotides. In some embodiments, the anchor sequence is at the 3' end of the oligonucleotide domain. In some embodiments, the anchor sequence is at the 5' end of the oligonucleotide domain.

In one additional embodiment, the biological particle capture regions 514 comprise a proteomic nucleic acid primer sequence that is configured to interact with a protein labeling agent that is used to label a population of fixed single biological particles (e.g., fixed single cells or fixed single nuclei) before or after contacting with the substrate. Such proteomic nucleic acid primer sequences can include a specific sequence that is complementary to a reporter oligonucleotide sequence conjugated to a protein labeling agent (e.g., an antibody). The reporter oligonucleotide sequence corresponds to the protein labeling agent used to label the fixed single biological particles. The proteomic nucleic acid primer sequence can prime a nucleic acid extension reaction to generate a nucleic acid molecule comprising the reporter oligonucleotide sequence, or a complement thereof. Additional methods and compositions concerning labeling agents with reporter oligonucleotides (comprising reporter sequences) are provided in WO/2018/119447, WO/2019/157529 US 20190338353, US 20200002763, and US 20190323088 each of which is incorporated by reference in its entirety.

Cell Capture Moieties of Cell Capture Regions

Referring to FIG. 5, the biological particle (e.g., cell or nucleus) capture moieties 508 of the biological particle capture regions 514 are designed to capture the single biological particles and to immobilize them during decrosslinking and hybridization. The biological particle capture moieties 508 are suitably located in a center region of the biological particle capture regions 514 and are suitably designed with a reverse transcription primer and barcoded to identify the biological particle capture regions 514, using any of the foregoing barcoding techniques. The biological particle capture moieties 508 can be formed by additionally coating and/or crosslinking the center regions of the biological particle capture regions 514 with a capturing molecule or compound that has a strong affinity for the single biological particles being targeted.

As explained above, the fixed biological particles (e.g. cells or nuclei) can be stained with a labelling agent that facilitates recognition and attachment to the biological particle capture moieties. When the fixed biological particles are so labelled, the biological particle capture moieties can be designed with a complementary biological particle capturing molecule or compound that will recognize, receive and attach to the fixed, stained biological particles. In one embodiment, the biological particle labelling agent can include a biotin compound that interacts with the analytes of the single biological particles (e.g., mRNA in the single cells) being analyzed and with the biological particle capture sites. Biotins bind easily to streptavidin, avidin and neutravidin protein molecules and such bonds are resistant to extreme heat, pH and proteolysis. The biological particle capture moieties 508 can therefore be designed by cross-linking or otherwise attaching streptavidin, avidin, and/or neutravidin to a suitably sized area in the center region of each biological particle capture region 514.

The biotin compound can be covalently attached to a protein, nucleic acid, or other molecule in the single biological particle (e.g. a cell or nucleus) being analyzed. The biotin can then bind the single biological particle to the streptavidin, avidin and neutravidin protein molecules in the capture site with high affinity, speed and specificity. This makes it possible to capture biotinylated molecules, and single biological particles stained with biotins, in a wide range of environments.

Other chemistries for the biological particle capture moieties 508 are also possible, so long as the design of the biological particle capture moieties 508 is compatible with the chemistry of the biological particles being captured in a manner that facilitates easy and strong attachment. The biological particle capture moieties 508 can embody the same chemistry as the corresponding barcoded oligonucleotides 510 located outside of the biological particle capture moiety 508, namely the inclusion of barcodes and a reverse transcription primer, with the addition of a compound, molecule or other moiety that has a strong affinity for the single biological particles (e.g., cells or nuclei) being captured.

In some examples, the biological particle capture moiety 508 can contain substances or molecules that can bind biological particles (e.g., cells or nuclei), thus retaining biological particles on a surface of a substrate. In some examples, such substances that are part of or contained with a biological particle capture moiety can bind specific biological particles (e.g., in the case of cells, antibodies binding a cellular antigen; a receptor molecule binding a ligand for the receptor). In some examples, such substances may bind biological particles nonspecifically (e.g., in the case of cells, bind any cell). In some examples, a biological particle capture moiety 508 can contain a substance configured to interact with a labeling agent that is used to label biological particles.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429 (Ser. No. 16/426,762); U.S. Pat. Publ. No. 2019/0177800 (Ser. No. 16/107,685); and U.S. Pat. Pub. Publ. No. 2019/0367969 (Ser. No. 16/375,093), which are each incorporated by reference herein in their entirety.

Fixing the Biological Particles

Biological samples are unstable. When a biological sample is removed from its viable niche or environment, physical decomposition begins immediately. The degree of decomposition is determined by a number of factors including time, solution buffering conditions, temperature, source (e.g. certain tissues and cells a have higher levels of endogenous RNase activity), biological stress (e.g. enzymatic tissue dissociation can activate stress response genes), and physical manipulation (e.g. pipetting, centrifuging). The degradation includes nucleic acid molecules (e.g., RNA), proteins, as well as higher-order 3D structure of molecular complexes, whole cells, tissues, organs, and organisms. The instability of biological samples is a significant obstacle for their use in a variety of assays, including droplet-based genomic assays. Sample degradation greatly limits the ability to use such assays accurately and reproducibly with a wide range of available biological samples.

Example methods for preserving biological sample integrity, and limiting decomposition include cryopreservation, dehydration (e.g., methanol), high salt storage (e.g., using RNAssist, or RNAlater®), and treatment with chemical fixing agents. Chemical fixing agents typically create covalently crosslinks in the biomolecules of the sample (e.g., paraformaldehyde). These techniques for stabilizing biological samples can be used alone or in combination, and each can be reversed to various extents using various un-fixing treatments.

The biological particle (e.g., cells or nuclei) are suitably provided as fixed single biological particles. The fixing can occur before and/or after dissociation of the individual biological particles from a biological fluid or biological tissue. The purpose of fixation is to preserve the biological particles from decay due to autolysis or putrefaction, and from degradation due to exposure to harsh conditions during processing.

The term "fixed" as used herein with regard to biological samples, and the tissues, biological particles (e.g., cells or nuclei) and molecules contained in the samples, refers to the state of being preserved from decay and/or degradation. "Fixation" refers to a process that results in a fixed sample, and can include contacting the biomolecules within a biological sample with a fixative (or fixing agent) for some amount of time, whereby the fixative results in covalent bonding interactions such as crosslinks between and within biomolecules in the sample. A "fixed biological sample" refers to a biological sample that has been contacted with a fixation reagent. For example, a formaldehyde-fixed biological sample has been contacted with the fixing agent formaldehyde.

Generally, contact of a biological particle (e.g., a cell or nucleus) from a biological sample with a fixing agent (e.g., paraformaldehyde or PFA) under appropriate conditions results in the formation of intra- and inter-molecular covalent crosslinks between biomolecules in the biological sample. In some cases, the fixation reagent, formaldehyde, is known to result in covalent aminal crosslinks in RNA, DNA, and/or protein molecules.

The amount of time a biological sample is contacted with a fixative to provide a fixed biological sample depends on the temperature, the nature of the sample, and the fixative used. For example, a biological sample can be contacted by a fixation agent for 72 or less hours (e.g., 48 or less hours, 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes). Various temperatures may be used during a fixation process.

Biological particles (e.g., cells or nuclei) can be fixed using any known fixing agent, including without limitation alcohols, ketones, aldehydes (e.g., glutaraldehyde), cross-linking agents, disuccinimidyl suberate (DSS), dimethylsuberimidate (DMS), formalin, dimethyladipimidate (DMA), dithio-bis(-succinimidyl propionate) (DSP), disuccinimidyl tartrate (DST), ethylene glycol bis (succinimidyl succinate) (EGS), bis(sulfosuccinimidyl)suberate (BS3) and combinations thereof. Also suitable are bis-imidazole-carboxylate compounds used to prepare reversibly fixed biological samples. Examples of fixing agents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

In some examples, a fixing agent is a formaldehyde-based fixing agent such as formalin, which is a mixture of formaldehyde and water. The formalin may include about 1% to about 15% by weight formaldehyde and about 85% to about 99% by weight water, suitable about 2% to about 8% by weight formaldehyde and about 92% to about 98% by weight water, or about 4% by weight formaldehyde and about 96% by weight water. In some examples, tissues may be fixed in 4% paraformaldehyde.

The fixing agents commonly act as crosslinking agents which create covalent chemical bonds between proteins in the biological particles (e.g., cells or nuclei). The fixed biological particles must typically be unfixed (decrosslinked) prior to single biological particle analysis, as further described below.

Other suitable fixing agents will be appreciated by those of ordinary skill in the art (e.g., U.S. Provisional Application No. 62/952,677, which is incorporated herein by reference in its entirety).

The formation of crosslinks in biomolecules (e.g., proteins, RNA, DNA) due to fixation greatly reduces the ability to detect (e.g., bind to, amplify, sequence, hybridize to) the biomolecules in standard assay methods. Common techniques to remove the crosslinks induced by fixative reagents (e.g., heat, acid) can cause further damage to the biomolecules (e.g., loss of bases, chain hydrolysis, cleavage, denaturation, etc.). Further description of the consequences of fixation of tissue samples and the benefits of removing adducts and/or crosslinks are described in U.S. Pat. No. 8,288,122, which is hereby incorporated by reference in its entirety. For example, the widely used fixing agent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity of proteins in the preserved tissue sample.

Modifying Biological Particles (Staining or Labelling) to Facilitate Attachment to Biological Particle Capture Moieties The methods and systems disclosed here use binding or attachment of single biological particles (e.g., cells or nuclei) to biological particle capture regions that have biological particle capture moieties and barcode molecules associated with the biological particle capture regions. The biological particle capture moieties retain the single biological particles.

The fixed biological particles (e.g., cells or nuclei) can be stained with a labelling agent that facilitates recognition and attachment to the biological particle capture sites. The biological particle labelling agent can be an agent that interacts both with the analyte (e.g., mRNA) in the single biological particles being analyzed and with the biological particle capture sites. Conjugated molecules that provide a biological particle labeling moiety and a different capture moiety may be used to label fixed single biological particles prior to analysis on a substrate as described herein. In one embodiment, the biological particle labelling moiety comprises a lipophilic moiety such as a cholesterol moiety. Those of ordinary skill in the art will appreciate that other biological particle labelling moieties may be suitable for use (e.g., US Publication 2020/0002763, which is incorporated herein by reference in its entirety) in the methods described herein. One suitable labeling technique, known as biotinylation, is accomplished by covalently attaching a biotin to a protein, nucleic acid, or other molecule in the biological particle being analyzed. The biotin can then bind to a selectively designed capture site with high affinity, speed and specificity. Various kinds of biotinylation include enzymatic biotinylation which allows biotin to be linked to a residue present in a protein, primary amine biotinylation which involves linkage of biotin to primary amine groups in the protein, sulfhydryl biotinylation which attaches biotin to sulfhydryl groups in the protein, carboxyl biotinylation which attaches biotin to carboxyl groups on the C-terminal ends of proteins and on glutamate and aspartate amino acid side chains, glycoprotein biotinylation which modifies the carbohydrate residues in glycoprotein to aldehydes that react with hydrazine- or alkoxyamine-based biotinylation reagents, oligonucleotide biotinylation which reacts oligonucleotides with biotin phosphoramidite, and non-specific biotinylation using photoactivatable biotin reagents. One example of a suitable biotin molecule for binding the fixed single cells or nuclei to the cell or nuclei capture sites is cholesterol-biotin.

Biotins bind easily to streptavidin, avidin and neutravidin protein molecules and such bonds are resistant to extreme heat, pH and proteolysis. This makes it possible to capture biotinylated molecules, and cells or nuclei stained with biotins, in a wide range of environments. Other forms of labeling can also be employed, including without limitation staining with 4-thiordine for the metabolic labeling of mRNA within the single biological particles being analyzed.

A variety of other molecular pairs can be used to bind cells to cell capture moieties. In some examples, the pairs may include glutathione and glutathione S-transferase, maltose and maltose-binding protein, and the SpyTag/SpyCatcher system, and the like. In some examples, antibodies designed to bind cells or specific types of calls may be part of the cell capture moiety.

In some instances, one or more labelling agents capable of binding to or otherwise coupling to one or more biological particle (e.g., cell or nucleus) features may be used to bind biological particles to a biological particle capture moiety. In some instances, biological particle features can include biological particle surface features. In the case of cells, cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429 (Ser. No. 16/426,762); U.S. Pat. Publ. No. 2019/0177800 (Ser. No. 16/107,685); and U.S. Pat. Pub. Publ. No. 2019/0367969 (Ser. No. 16/375,093), which are each incorporated by reference herein in their entirety.

The fixed biological particles (e.g., cells or nuclei) can also be stained with various other staining agents, including without limitation acridine orange, Bismarck brown, carmine, Coomassie blue, cresyl violet, 4,6-diamidino-2-phenylindole (DAPI), eosin, hematoxylin, hematoxylin & eosin (H&E), ethidium bromide, acid fuchsine, iodine, methyl green, bisbenzimides, iodine, methyl green, methylene blue, neutral red, Nile blue, Nile red, osmium tetroxide, propidium iodide, rhodamine, safrain, radioisotopes, fluorophores, chemiluminescent compounds, bioluminescent compounds, and combinations thereof.

Attachment of the Single Biological Particles to the Biological Particle Capture Moieties Attachment of the fixed single biological particles (e.g., cells or nuclei) to the biological particle attachment sites can be accomplished by any suitable means and will depend on the specific chemistry and design of the biological particles and the biological particle capture sites. For example, the affinity between streptavidin and biotin is among the strongest noncovalent biological interactions known, with a dissociation constant $K_d$ in the femtomolar range. Thus, when the single biological particles (e.g., cells or nuclei) are labelled (biotinylated) with a suitable biotin compound such as cholesterol-biotin, and when the biological particle capture sites are formed using streptavidin, the attachment between the single biological particles and the biological particle capture sites will occur rapidly and spontaneously upon contact. By applying a suspension of the fixed single biological particles to the surface containing the biological particle capture regions, the slide surface can be effectively covered with single biological particles bound to individual biological particle capture moieties.

Generally, a single fixed biological particle (e.g., a cell or nucleus) is to be retained by one biological particle capture moiety. In that way, barcoded oligonucleotides having capture domains that surround the biological particle capture moiety can capture the analytes from the single retained biological particle.

In some examples, a solution containing the fixed biological particles (e.g., cells or nuclei) can be contacted with the biological particle capture regions. In some examples, the biological particle contacting can be performed by flowing a population of biological particles in a solution over the disclosed systems. By adjusting the concentration of biological particles in the solution, one can increase the probability that a biological particle capture moiety will retain a biological particle, and will not retain greater than one biological particle (e.g., Poisson statistics). In some examples, the biological particle capture moieties may be designed such that, once a single biological particle is retained by the biological particle capture moiety, additional biological particles are excluded from being retained.

Immobilizing the Single Biological Particles and their Contents

The fixed single biological particles (e.g., cells or nuclei) can be effectively immobilized by their contact and interaction with the biological particle capture moieties. However further, generally optional steps can be taken to immobilize the contents of the individual biological particles, such as the mRNA (from cells or nuclei), which might otherwise leak and migrate during decrosslinking and subsequent hybridization of the single biological particles. This can be accomplished by covering the biological particle capture moieties and attached single biological particles with a thin polymer membrane coating that is permeable to a decrosslinking agent but tends to immobilize the biological particle contents such as mRNA within the vicinity of the capture moieties. The thin polymer membrane can be but does not have to be impermeable to the mRNA within the biological particles. Because the substrates supporting the biological particle capture regions are typically laid flat on a horizontal surface, the decrosslinking agent can easily migrate downward through the permeable membrane, and the mRNA will not readily migrate upward against the force of gravity.

The permeable polymer membrane can be a porous membrane having microscopic pores, or a nonporous membrane having intermolecular spaces through which a decrosslinking agent can diffuse. Suitable polymers include without limitation polydimethyl siloxane, polycarbonate, polyethylene terephthalate, polylactic acid, polycaprolactone, polyamides, dichloro[2,2]paracyclophane, polytetrafluoroethylene, poly(urethane acrylate), poly(ethylene glycol) diacrylate, and combinations thereof. The permeable polymer membrane need not be very thick and may have a thickness ranging from less than one micron to about 50 microns, or from about 1 micron to about 10 microns. The permeable polymer membrane need only cover the biological particle (e.g., cell or nucleus) capture moieties with attached biological particles, and the immediately surrounding areas. However, for the sake of convenience, the thin polymer membrane can be laminated over the entire biological particle capture regions, or even over the entire substrate surface that includes the multiple biological particle capture regions.

Decrosslinking the Single Biological Particles

The ability to use a fixed biological sample in various assays requires rapid and efficient un-fixing of the sample to obtain the relevant genomic assay information before degradation of the sample occurs. Ideally, the assay data obtained from an un-fixed biological sample should be identical to that obtained from a fresh sample that has not been fixed, or resemble a sample obtained from its natural environment as closely as possible.

Conditions for reversing the effects of fixing a biological sample are known in the art, however, these conditions tend to be harsh. See e.g., WO2001/46402; US2005/0014203A1, and US2009/0202998A1, each of which is hereby incorporated by reference in its entirety. For example, un-fixing treatment of PFA-treated tissue samples includes heating to 60-70° C. in Tris buffer for several hours, and yet typically results in removal of only a fraction of the fixative-induced crosslinks. Furthermore, the harsh un-fixing treatment conditions can result in permanent damage to biomolecules, particularly nucleic acids, in the sample. Recently, less harsh un-fixing techniques and conditions have been proposed that utilize compounds capable of chemically reversing the crosslinks resulting from fixation. See e.g., Karmakar et al., "Organocatalytic removal of formaldehyde adducts from RNA and DNA bases," Nature Chemistry, 7: 752-758 (2015); US 2017/0283860A1; and US 2019/0135774A1, each of which is hereby incorporated by reference in its entirety.

The terms "un-fixing agent" (or "decrosslinking agent") as used herein, refer to a compound or composition that reverses fixation and/or removes the crosslinks within or between biomolecules in a sample caused by previous use of a fixation reagent. In some embodiments, un-fixing agents are compounds that act catalytically to remove or break crosslinks in a fixed sample.

In some examples, the un-fixing agents are proteases. Various proteases may be used. Proteases used in the present disclosure may include serine proteases, cysteine proteases, threonine proteases, aspartic proteases, glutamic proteases, metalloproteases, asparagine peptide lyases, and others. Proteases used in the compositions, methods, reagents and kits disclosed here may come from many different organisms. The proteases may be variants of or derived from other proteases.

In some examples, the protease is Proteinase K. In some examples, the protease is a subtilisin. In some examples, the protease is subtilisin A. Combinations of proteases may be used.

In some examples, the un-fixing agents may include substances such as 2-amino-5-methylbenzoic acid, 2-amino-5-nitrobenzoic acid, (2-amino-5-methylphenyl)phosphonic acid, 2-amino-5-methylbenzenesulfonic acid, 2,5-diaminobenzenesulfonic acid, 2-amino-3,5-dimethylbenzenesulfonic acid, (2-amino-5-nitrophenyl)phosphonic acid, (4-aminopyridin-3-yl)phosphonic acid, and (2-amino-5-{[2-(2-poly-ethoxy)ethyl]carbamoyl}phenyl)phosphonic acid.

In some examples, un-fixing reactions may be performed on fixed cells as follows. Unattached cells are fixed with 4% PFA for 24 h at 4° C. and quenched with 10% Fetal Bovine Serum ("FBS") in PBS. Un-fixing agents are prepared in a buffer at neutral pH. The concentration of the un-fixing agent(s) may be titrated to obtain desired results. The fixed cells are treated with the un-fixing agent solution, for example, at 40° C. for 2 hours. The reaction may also contain one or more RNase inhibitors. After the treatment, the reaction volume may be centrifuged to pellet the cells. Biomolecules (e.g., RNA) may be collected from the cell pellet and/or the supernatant of the centrifugation, using standard methods, and quantified. Success of the un-fixing, at least as it relates to RNA un-fixing, may be measured by both the amount of RNA that is recovered, and the ability of the recovered RNA to function as a substrate or template in various enzymatic reactions. In some examples, the ability of the recovered RNA to serve as template for production of suitable sequence libraries may be determined and serve as an indicator of the results obtained from the un-fixing reaction.

Decrosslinking (un-fixing) of the fixed single biological particles (e.g., cells or nuclei) retained by biological particle capture regions, part or all of which are covered with permeable polymers, can be accomplished by first applying a de-crosslinking agent over the permeable polymer membrane coating and allowing it to diffuse through the permeable membrane and contact the fixed immobilized single biological particles attached to their respective biological particle capture moieties. The amount and type of crosslinking agent can vary depending on the biological particle type, the fixation technique employed, and other variables. Suitable decrosslinking agents include without limitation a compound capable of cleaving a carbamate bond, a compound capable of cleaving a disulfide bond, a compound capable of reversing formaldehyde fixation, and combinations thereof. Compounds capable of cleaving a carbamate bond include without limitation diethylene triamine (DETA), ethylene diamine (EDA), hydrazine monohydrate, and combinations thereof. Compounds capable of cleaving a disulfide bond include without limitation dithiothreitol (DTT), iodoacetamine, and combinations thereof. Compounds capable of reversing formaldehyde fixation include without limitation proteinase K, sodium dodecyl sulfate, sodium chloride, and combinations thereof. Other suitable decrosslinking agents will be appreciated by those of ordinary skill in the art (e.g., U.S. Provisional Application No. 62/952,670, which is incorporated herein by reference in its entirety).

Because decrosslinking involves an endothermic reaction, it requires the application of significant heat and time. For example, the decrosslinking can require temperatures of about 30° C. to about 70° C., or about 40° C. to about 60° C., and can require exposure times of about 5 minutes to about 30 minutes, or about 10 minutes to about 20 minutes. The temperature and times required for decrosslinking can vary depending on the biological particle type (e.g., cell type), the fixation technique employed, and other variables. These conditions, coupled with the chemical reactions involved, are relatively harsh and can result in leakage of mRNA and related analyte components from the immobilized single biological particles (e.g., cells or nuclei). When this occurs, the permeable polymer membrane covering the captured single biological particles maintain most of the dissociated mRNA at the locations of the captured single biological particles. Any dissociated mRNA that penetrates the permeable polymer membrane does so against the force of gravity and will then be reabsorbed and ultimately hybridized to cDNA in the areas of the biological particle capture regions immediately surrounding the biological particle capture moieties. The dissociated mRNA is thus prevented from leaving the immediate vicinity of the respective captured single biological particles and is prevented from migrating to the neighboring barcoded spots and captured single biological particles.

Capture of Analytes from the Single Biological Particles

Once the fixed single biological particles (e.g., cells or nuclei) have been decrosslinked, the captured single biological particles can be washed to remove excess decrosslinking agent. Washing can be accomplished using a mild buffering solution such as a phosphate buffer solution (PBS), for example, a solution of 1×PBS available from 10X Genomics, or a saline sodium citrate (SSC) buffer, for example, a solution of 0.1×SSC. Other washing solutions can also be employed.

In one embodiment, the analyte of interest is mRNA and hybridization occurs via capture of mRNA from the captured fixed single biological particle (e.g., cell or nucleus) by an analyte binding sequence (i.e., capture domain) involving a reverse transcription of the mRNA in the single biological particle and the oligonucleotide domain of the reverse transcription primer to yield cDNA, which can then be analyzed. The hybridization can proceed using techniques that are known from the field of spatial transcriptomics. A detailed description of one suitable hybridization protocol and subsequent analysis is provided in the Visium Spatial Gene Expression Reagent Kits User Guide, Rev. A, published by 10X Genomics, which is incorporated herein by reference. Preferably, the reverse transcription primer described above is provided with a fluorescent oligonucleotide capture domain that results in production of fluorescent cDNA during the reverse transcription process. Although fluorescent oligonucleotide capture domains are not required, their use facilitates improved analysis of the cDNA. The hybridization can be facilitated via incubation of the immobilized single biological particle (e.g., cells or nuclei) at a moderately elevated temperature of about 30° C. to about 60° C., suitably about 35° C. to about 50° C., or about 40° C. to about 45° C., for a time period of about 15 minutes to about 75 minutes, suitably about 30 minutes to about 60 minutes, or about 40 minutes to about 50 minutes. Preferred hybridization conditions may vary depending on the type of single biological particle and the reverse transcription primer that is used.

The hybridization yields cDNA footprints on the surface at the locations of the biological particle (e.g., cell or nucleus) capture regions. The cDNA footprints can then be imaged and analyzed using techniques known from spatial transcriptomics, including the molecular barcoding and imaging techniques known from the aforementioned Visium Spatial Gene Expression Reagent Kits User Guide, published by 10X Genomics. The inventive method allows for the molecular barcoding and/or imaging analysis of a large number of single immobilized biological particles (e.g., cells or nuclei) simultaneously on a single slide surface. For example, a 6.5 mm×6.5 mm area can accommodate at least 5000 isolated immobilized single biological particles. A 13 mm×13 mm area can accommodate at least 20,000 of the immobilized single biological particles. A 13 mm×26 mm area can accommodate at least 40,000 of the immobilized single biological particles and a 13 mm×39 mm area can accommodate at least 60,000 of the immobilized single biological particles.

In some examples, a plurality of molecules are generated from barcoded molecules that have bound analytes. Generally, the generated molecules contain copies of the barcodes or barcode sequences contained in the barcode molecules. This may be done enzymatically, in some examples using reverse transcriptases and polymerases. Libraries may be created using the generated molecules. Nucleotide sequences of the libraries may be obtained.

The invention also provides a corresponding system for capturing and analyzing single biological particles (e.g., cells or nuclei). The system includes a reverse transcription microscope slide having a surface, as described above; a plurality of barcoded spots attached to the surface, as described above; a barcoded capture site attached to each barcoded spot, as described above; and a permeable polymer membrane over each barcoded capture site, as described above; wherein the permeable polymer membrane immobilizes a single biological cell within the respective capture site and is permeable to a reverse crosslinking agent.

Embodiments of the invention, which are not meant to be limiting, are described in the numbered paragraphs below. The embodiments of the invention described herein are exemplary, and various modifications and improvements can be made without departing from the spirit and scope of the invention. The scope of the invention is defined by the appended claims, and all changes that fall within the meaning and range of equivalents are intended to be embraced therein.

1. A method of analyzing single biological particles (such as cells or nuclei), comprising the steps of:
providing a quantity of fixed single biological cells;
individually attaching the fixed single biological cells to a plurality barcoded spots on a surface;
immobilizing the fixed single biological cells on the surface by applying a permeable polymer coating over the fixed single biological cells;
applying a reverse crosslinking agent to the polymer coating, wherein the reverse crosslinking agent permeates the polymer coating to decrosslink the fixed single biological cells, yielding single biological cells;
hybridizing mRNA originating from the single biological cells on the surface using a reverse transcription primer associated with the barcoded spots; and
imaging the hybridized mRNA from the single biological cells.

2. The method of paragraph 1, wherein the single biological cells are fixed using an organic fixing agent selected from the group consisting of an alcohol, ketone, aldehyde, cross-linking agent, disuccinimidyl suberate (DSS), dimethylsuberimidate (DMS), formalin, dimethyladipimidate (DMA), dithio-bis(-succinimidyl propionate) (DSP), disuccinimidyl tartrate (DST), ethylene glycol bis (succinimidyl succinate) (EGS), bis-imidazole-carboxylate compounds, and combinations thereof.

3. The method of paragraph 2, wherein the organic fixing agent comprises formalin.

4. The method of paragraph 1, wherein each barcoded spot comprises a cell capture site and barcodes printed over the cell capture site to identify the barcoded spot.

5. The method of paragraph 4, further comprising the step of staining the fixed single biological cells with a labelling agent that facilitates attachment of the fixed single biological cells to capture sites on the barcoded spots.

6. The method of paragraph 5, wherein the labelling agent comprises a biotinylated compound.

7. The method of paragraph 1, wherein the barcoded spot has a diameter of about 15 to about 150 microns.

8. The method of paragraph 1, wherein the barcoded spot has a diameter of about 30 to about 80 microns.

9. The method of paragraph 4, wherein the cell capture site has a diameter of about 1 to about 15 microns.

10. The method of paragraph 4, wherein the cell capture site comprises a protein selected from the group consisting of streptavidin, avidin, neutravidin, and combinations thereof.

11. The method of paragraph 1, wherein the surface is a surface of a reverse transcription microscope slide.

12. The method of paragraph 1, wherein the barcoded spots comprise barcodes selected from the group consisting of polynucleotide barcodes, random nucleic acid sequences, amino acid sequences, synthetic nucleic acid sequences, synthetic amino acid sequences, and combinations thereof.

13. The method of paragraph 4, wherein the barcodes are selected from the group consisting of polynucleotides, random nucleic acid sequences, amino acid sequences, synthetic nucleic acid sequences, synthetic amino acid sequences, and combinations thereof.

14. The method of paragraph 13, wherein the barcodes are attached to an mRNA molecule.

15. The method of paragraph 1, wherein the barcoded spots comprise fluorescent barcodes to which fluorescently labeled oligonucleotide probes hybridize.

16. The method of paragraph 1, wherein the polymer coating comprises a permeable membrane selected from the group consisting of polydimethyl siloxane, polycarbonate, polyethylene terephthalate, polylactic acid, polycaprolactone, polyamides, dichloro[2,2]paracyclophane, polytetrafluoroethylene, poly(urethane acrylate), poly(ethylene glycol) diacrylate, and combinations thereof.

17. The method of paragraph 1, wherein the reverse crosslinking agent is selected from the group consisting of a compound capable of cleaving a carbamate bond, a compound capable of cleaving a disulfide bond, a compound capable of reversing formaldehyde fixation, and combinations thereof 18. The method of paragraph 17, wherein the reverse crosslinking agent comprises a compound capable of cleaving a carbamate bond selected from the group consisting of diethylene triamine (DETA), ethylene diamine (EDA), hydrazine monohydrate, and combinations thereof.

19. The method of paragraph 17, wherein the reverse crosslinking agent comprises a compound capable of cleaving a disulfide bond selected from the group consisting of dithiothreitol (DTT), iodoacetamine, and combinations thereof.

20. The method of paragraph 17, wherein the reverse crosslinking agent is a compound capable of reversing formaldehyde fixation selected from the group consisting of proteinase K, sodium dodecyl sulfate, sodium chloride, and combinations thereof.

21. The method of paragraph 1, further comprising the step of applying heat to the reverse crosslinking agent to facilitate decrosslinking of the fixed single biological cells.

22. The method of paragraph 1, wherein the reverse transcription primer comprises a functional nucleic acid sequence configured to interact with target mRNA molecules.

23. The method of paragraph 22, wherein the functional nucleic acid sequence comprises a poly(T) sequence.

24. The method of paragraph 1, wherein the reverse transcription primer associated with the barcoded spots comprises a barcoded reverse transcription primer.

25. The method of paragraph 1, wherein the reverse transcription primer comprises one or more of ribonucleotides, deoxyribonucleotides and synthetic nucleotide residues that can participate in base pair interactions with target mRNA molecules.

26. The method of paragraph 1, wherein the reverse transcription primer comprises a splint oligonucleotide sequence.

27. The method of paragraph 1, wherein the reverse transcription primer comprises a random oligonucleotide sequence.

28. The method of paragraph 1, wherein the reverse transcription primer comprises an oligo-deoxythymine (oligo-dT) sequence.

29. The method of paragraph 1, further comprising the step of washing the reverse crosslinking agent from the single biological cells prior to hybridization.

30. A method of analyzing single biological cells, comprising the steps of:
providing a quantity of fixed single biological cells;
attaching the fixed single biological cells to barcoded cell capture sites;
immobilizing the fixed single biological cells on the barcoded cell capture sites;
decrosslinking the fixed single biological cells, yielding single biological cells;
hybridizing mRNA originating from the single biological cells using a reverse transcription primer; and
imaging the hybridized mRNA from the single biological cells.

31. The method of paragraph 30, wherein each cell capture site has a diameter of about 1 to about 15 microns.

32. The method of paragraph 30, wherein each cell capture site has a diameter of about 5 to about 10 microns.

33. The method of paragraph 30, wherein each cell capture site captures only one fixed single biological cell.

34. The method of paragraph 30, wherein each cell capture site comprises a protein.

35. The method of paragraph 34, wherein the protein is selected from the group consisting of streptavidin, avidin, neutravidin, and combinations thereof.

36. The method of paragraph 30, wherein the step of immobilizing the fixed single biological cells on the surface comprises applying a polymer coating over the fixed single biological cells attached to the barcoded cell capture site, wherein the polymer coating is permeable to the reverse crosslinking agent.

37. The method of paragraph 36, wherein the polymer coating comprises a permeable membrane selected from the group consisting of polydimethyl siloxane, polycarbonate, polyethylene terephthalate, polylactic acid, polycaprolactone, polyamides, dichloro[2,2]paracyclophane, polytetrafluoroethylene, poly(urethane acrylate), poly(ethylene glycol) diacrylate, and combinations thereof.

38. The method of paragraph 30, wherein the single biological cells are fixed using an organic fixing agent selected from the group consisting of an alcohol, ketone, aldehyde, cross-linking agent, disuccinimidyl suberate (DSS), dimethylsuberimidate (DMS), formalin, dimethyladipimidate (DMA), dithio-bis(-succinimidyl propionate) (DSP), disuccinimidyl tartrate (DST), ethylene glycol bis (succinimidyl succinate) (EGS), bis-imidazole-carboxylate compounds, and combinations thereof.

39. The method of paragraph 38, wherein the decrosslinking is accomplished using a reverse crosslinking agent capable of cleaving a carbamate bond and selected from the group consisting of diethylene triamine (DETA), ethylene diamine (EDA), hydrazine monohydrate, and combinations thereof.

40. The method of paragraph 38, wherein the decrosslinking is accomplished using a reverse crosslinking agent capable of cleaving a disulfide bond and selected from the group consisting of dithiothreitol (DTT), iodoacetamine, and combinations thereof.

41. The method of paragraph 38, wherein the decrosslinking is accomplished using a reverse crosslinking agent capable of reversing formaldehyde fixation and selected from the group consisting of proteinase K, sodium dodecyl sulfate, sodium chloride, and combinations thereof.

42. The method of paragraph 30, further comprising the step of applying heat to facilitate decrosslinking of the fixed single biological cells.

43. The method of paragraph 30, wherein the barcoded cell capture sites comprise barcodes selected from the group consisting of polynucleotide barcodes, random nucleic acid sequences, amino acid sequences, synthetic nucleic acid sequences, synthetic amino acid sequences, and combinations thereof.

44. The method of paragraph 43, wherein the barcodes are attached to an mRNA molecule.

45. The method of paragraph 30, wherein the barcoded cell capture sites comprise fluorescent barcodes to which fluorescently labeled oligonucleotide probes hybridize.

46. The method of paragraph 30, wherein the reverse transcription primer comprises a functional nucleic acid sequence configured to interact with target mRNA molecules.

47. The method of paragraph 46, wherein the functional nucleic acid sequence comprises a poly(T) sequence.

48. The method of paragraph 30, wherein the reverse transcription primer comprises one or more of ribonucleotides, deoxyribonucleotides and synthetic nucleotide residues that can participate in base pair interactions with target mRNA molecules.

49. The method of paragraph 30, wherein the reverse transcription primer comprises a splint oligonucleotide sequence.

50. The method of paragraph 30, wherein the reverse transcription primer comprises a random oligonucleotide sequence.

51. The method of paragraph 30, wherein the reverse transcription primer comprises an oligo-deoxythymine (oligo-dT) sequence.

52. The method of paragraph 30, further comprising the step of washing the reverse crosslinking agent from the single biological cells prior to hybridization.

53. The method of paragraph 30, further comprising the step of staining the fixed single biological cells.

The invention claimed is:

1. A method of analysis for aldehyde fixed cells comprising:
   providing a substrate comprising a plurality of capture regions, wherein a capture region of the plurality of capture regions comprises:
   a plurality of antibodies capture moiety and a plurality of barcode molecules, wherein a barcode molecule of the plurality of barcode molecules comprises a common barcode sequence and an analyte a nucleic acid binding sequence;
   contacting a plurality of aldehyde fixed cells with the substrate, wherein an aldehyde fixed cell of the plurality of aldehyde fixed cells binds to an antibody of the plurality of antibodies, thereby generating a captured aldehyde fixed cell at the capture region;
   applying a polydimethyl siloxane permeable coating to the substrate, thereby immobilizing the captured aldehyde fixed cell;
   reversing fixation of the aldehyde captured fixed cell at the capture region to release a plurality of nucleic acids from the captured aldehyde fixed cell and hybridizing a nucleic acid of the plurality of nucleic acids to the nucleic acid binding sequence of the barcode molecule; and
   generating a plurality of barcoded molecules from the plurality of nucleic acids and the plurality of barcode molecules, wherein a barcoded molecule of the plurality of barcoded molecules comprises the common barcode sequence, or a complement thereof, and a sequence corresponding to the nucleic acid, or a complement thereof.

2. The method of claim 1, wherein the common barcode sequence is unique to the capture region.

3. The method of claim 1, wherein the nucleic acid binding sequence comprises a poly(dT) sequence, a random sequence or a targeted sequence.

4. The method of claim 1, wherein the plurality of aldehyde fixed cells comprises a plurality of labeled aldehyde fixed cells.

5. The method of claim 4, wherein a labeled aldehyde fixed cell of the plurality of labeled aldehyde fixed cells includes comprises a label, wherein the label comprises a labeling moiety and a protein.

6. The method of claim 5, wherein the capture region of the plurality of capture regions comprises the antibody which specifically binds to the protein.

7. The method of claim 5, wherein the labeling moiety comprises a moiety selected from the group consisting of a lipid, a dye, a peptide, an antibody, and a nanoparticle.

8. The method of claim 1, wherein the plurality of nucleic acids comprises RNA.

9. The method of claim 8, wherein the plurality of nucleic acids comprise messenger RNA (mRNA).

10. The method of claim 1, further comprising providing a protein binding agent to the aldehyde fixed cell, wherein the protein binding agent is capable of specifically binding to a polypeptide from the aldehyde fixed cell.

11. The method of claim 10, wherein the protein binding agent comprises a reporter molecule corresponding to the protein binding agent.

12. The method of claim 11, wherein the reporter molecule is an oligonucleotide comprising a reporter sequence.

13. The method of claim 12, wherein the nucleic acid binding sequence comprises a sequence that is complementary to the reporter sequence.

14. The method of claim 10, wherein the protein binding agent is provided prior to contacting the plurality of aldehyde fixed cells with the substrate.

15. The method of claim 10, wherein the protein binding agent comprises an antibody.

16. The method of claim 1, wherein the barcode molecule further comprises a unique molecular identifier.

17. The method of claim 1, wherein generating the barcoded molecule from the nucleic acid of the plurality of nucleic acids comprises extending the barcode molecule.

18. The method of claim 17, wherein the extending comprises use of a reverse transcriptase or a polymerase.

19. The method of claim 18, further comprising determining the sequence of the common barcode sequence, or a complement thereof, and all or a portion of the nucleic acid, or a complement thereof.

* * * * *

UNITED STATES PATENT AND TRADEMARK OFFICE
CERTIFICATE OF CORRECTION

| | | |
|---|---|---|
| PATENT NO. | : 11,926,863 B1 | Page 1 of 1 |
| APPLICATION NO. | : 17/187227 | |
| DATED | : March 12, 2024 | |
| INVENTOR(S) | : Stephane Boutet | |

It is certified that error appears in the above-identified patent and that said Letters Patent is hereby corrected as shown below:

In the Claims

Column 32, Line 3, in Claim 5, before "comprises" delete "includes".

Signed and Sealed this
Twenty-first Day of May, 2024

Katherine Kelly Vidal
*Director of the United States Patent and Trademark Office*